US011155780B2

(12) United States Patent
Church et al.

(10) Patent No.: US 11,155,780 B2
(45) Date of Patent: Oct. 26, 2021

(54) METASTABLE STATE MIXING

(71) Applicant: NCH Life Sciences LLC, Irving, TX (US)

(72) Inventors: Jordan E. Church, Dallas, TX (US); Gabriel F. K. Everett, Mansfield, TX (US); Charles J. Greenwald, Irving, TX (US); Christopher J. Laney, Euless, TX (US); Michael Paloian, Cold Spring Harbor, NY (US); Judith G. Pruitt, Mesquite, TX (US); Amanda K. Rosmarin, Lantana, TX (US); Michael J. Schuster, Shorewood, IL (US)

(73) Assignee: NCH Life Sciences LLC, Irving, TX (US)

( * ) Notice: Subject to any disclaimer, the term of this patent is extended or adjusted under 35 U.S.C. 154(b) by 109 days.

(21) Appl. No.: 16/151,165

(22) Filed: Oct. 3, 2018

(65) Prior Publication Data

US 2019/0100723 A1 Apr. 4, 2019

Related U.S. Application Data

(60) Provisional application No. 62/568,007, filed on Oct. 4, 2017.

(51) Int. Cl.

*C12N 1/20* (2006.01)
*A61K 35/742* (2015.01)
(Continued)

(52) U.S. Cl.

CPC .............. *C12N 1/20* (2013.01); *A61K 35/742* (2013.01); *C12M 29/00* (2013.01); *C12M 41/12* (2013.01);
(Continued)

(58) Field of Classification Search

CPC ............ C12N 1/20; C12N 3/00; C12M 29/00; C12M 41/12; C12M 41/48; C12M 45/22; A61K 35/742; B01J 8/008; B01J 8/0015
See application file for complete search history.

(56) References Cited

U.S. PATENT DOCUMENTS

| | | | |
|---|---|---|---|
| 4,696,902 | A | 9/1987 | Bisconte |
| 6,790,355 | B2 | 9/2004 | Shaffer et al. |

(Continued)

FOREIGN PATENT DOCUMENTS

| | | | |
|---|---|---|---|
| KR | 100865682 | B1 | 10/2008 |
| WO | 02/055441 | A1 | 7/2002 |
| WO | 2017/117089 | A1 | 7/2017 |

OTHER PUBLICATIONS

International Search Report dated Dec. 11, 2018.

(Continued)

*Primary Examiner* — Michael L Hobbs
(74) *Attorney, Agent, or Firm* — Thomas | Horstemeyer LLP

(57) ABSTRACT

Metastable state spore incubation mixing systems are described. An example system includes a spore container to store spores, a nutrient container, an arrangement of valves and tubes, a reciprocating pump, a mixing tube, and a holding tank. In a drawing phase of the system, a controller can control the reciprocating pump to draw a ratioed volume of the spores, the nutrients, and water through the valves and tubes. During an expelling phase of the system, the controller can control flow control valves to direct the spores, nutrients, and water through the mixing tube and into the holding tank. The controller can also direct a heater to heat the mixture in the holding tank to a predetermined temperature. Once the mixture reaches the temperature, the control-
(Continued)

ler can also direct the system through a number of other phases of operation, including cooling and purging phases.

20 Claims, 15 Drawing Sheets

(51) Int. Cl.

| | |
|---|---|
| ***C12M 1/34*** | (2006.01) |
| ***C12N 3/00*** | (2006.01) |
| ***C12M 1/00*** | (2006.01) |
| ***C12M 1/36*** | (2006.01) |
| *B01J 8/00* | (2006.01) |

(52) U.S. Cl.
CPC ............ *C12M 41/48* (2013.01); *C12M 45/22* (2013.01); *C12N 3/00* (2013.01); *B01J 8/008* (2013.01); *B01J 8/0015* (2013.01)

(56) References Cited

U.S. PATENT DOCUMENTS

| | | | |
|---|---|---|---|
| 6,982,032 | B2 | 1/2006 | Shaffer et al. |
| 7,022,234 | B2 | 4/2006 | Shaffer et al. |
| 8,822,208 | B2 | 9/2014 | Chokshi |
| 2002/0179525 | A1 | 12/2002 | Shaffer et al. |
| 2002/0189997 | A1 | 12/2002 | Shaffer et al. |
| 2003/0029793 | A1 | 2/2003 | Shaffer et al. |
| 2004/0016697 | A1 | 1/2004 | Shaffer et al. |
| 2004/0232069 | A1 | 11/2004 | Shaffer et al. |
| 2009/0137029 | A1 | 5/2009 | Breidenthal et al. |
| 2009/0145070 | A1* | 6/2009 | Linn ........................ E04B 1/355 52/465 |
| 2009/0242173 | A1 | 10/2009 | Mitchell et al. |
| 2010/0261226 | A1* | 10/2010 | Niazi ..................... C12M 23/26 435/40 |
| 2012/0034344 | A1 | 2/2012 | Menon et al. |
| 2013/0224358 | A1 | 8/2013 | Michel et al. |
| 2017/0029760 | A1 | 2/2017 | Niu |
| 2017/0175070 | A1* | 6/2017 | Boyette .................. C12M 41/48 |
| 2018/0057783 | A1 | 3/2018 | Paldus et al. |
| 2018/0320122 | A1 | 11/2018 | Blanchard |
| 2019/0002819 | A1 | 1/2019 | Heffron |

OTHER PUBLICATIONS

First Examination Report for Indian Patent Application No. 202017016164 dated Oct. 10, 2020.

Office Action for Colombial Patent Application No. NC2020/0011926 dated Mar. 10, 2021.

Office Action for Canadian Patent Application No. 3,077,364 dated May 25, 2021.

Examination Report dated Jul. 29, 2021 for New Zealand Application No. 763367.

Extended European Search Report for European Patent Application No. 18865084.0 dated May 27, 2021.

P. Setlow, Germination of Spores of Bacillus Species: What We Know and Do Not Know, Journal of Bacteriology (Print), Jan. 31, 2014, pp. 1297-1305, vol. 196, No. 7, Department of Molecular Biology and Biophysics, University of Connecticut Health Center, Framington, Connecticut, USA.

* cited by examiner

50

```
                    START
                      │
                      ▼
┌─────────────────────────────────────────────────────────┐
│ Draw a volume of spores, nutrients, and water through   │
│ valves and tubes into the reciprocating pump            │
│                        803                              │
└─────────────────────────────────────────────────────────┘
                      │
                      ▼
┌─────────────────────────────────────────────────────────┐
│ Expel the spores, nutrients, and water from the         │
│ reciprocating pump                                      │
│                        806                              │
└─────────────────────────────────────────────────────────┘
                      │
                      ▼
┌─────────────────────────────────────────────────────────┐
│ Mix the spores, nutrients, and water together in a      │
│ mixing tube                                             │
│                        809                              │
└─────────────────────────────────────────────────────────┘
                      │
                      ▼
┌─────────────────────────────────────────────────────────┐
│ Direct the mixture of the spores, nutrients, and water  │
│ to a holding tank                                       │
│                        812                              │
└─────────────────────────────────────────────────────────┘
                      │
                      ▼
┌─────────────────────────────────────────────────────────┐
│ Heat the mixture of the spores, nutrients, and water    │
│ in the holding tank                                     │
│                        815                              │
└─────────────────────────────────────────────────────────┘
                      │
                      ▼
                     END
```

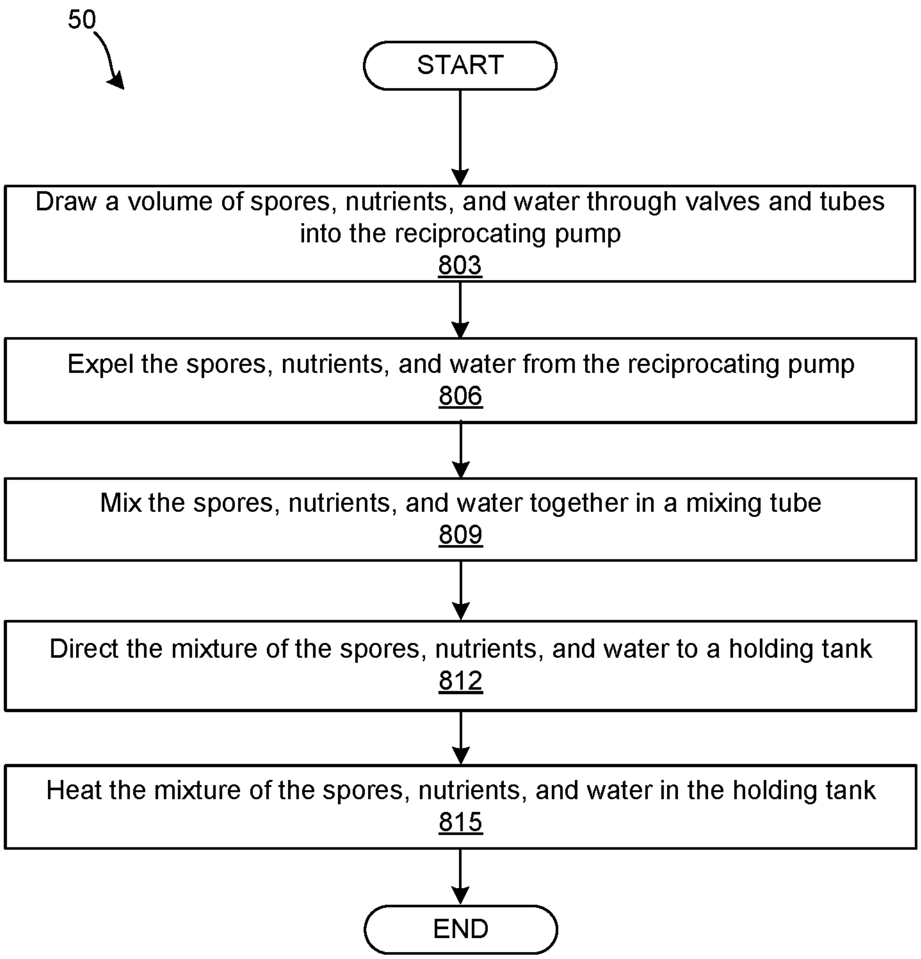

FIG. 8

METASTABLE STATE MIXING

CROSS-REFERENCE TO RELATED APPLICATIONS

This application claims the benefit of U.S. Provisional Application No. 62/568,007, filed Oct. 4, 2017, the entire contents of which is hereby incorporated herein by reference.

BACKGROUND

Bacterial spore germination is a multistep process wherein spores effectively wake-up or are revived from a dormant state to a vegetative growth state. The germination process is typically initiated by an environmental signal called a germinant which can be a nutrient such as an L-amino acid or a sugar. Additionally, germination can be accelerated by the addition of heat. Here, a device is described that allows for germination of *Bacillus* species using a nutrient germinant composition and heat in a single step at a point-of-use location where the bacteria will be distributed to a consumer/user, for example, in the way of a probiotic for use in animals.

BRIEF DESCRIPTION OF THE DRAWINGS

Aspects of the present disclosure can be better understood with reference to the following drawings. It is noted that the elements in the drawings are not necessarily to scale, with emphasis instead being placed upon clearly illustrating the principles of the embodiments. In the drawings, like reference numerals designate like or corresponding, but not necessarily the same, elements throughout the several views.

FIG. 8 is a flowchart illustrating examples of functionality implemented as portions of a controller operating in the metastable state spore incubation mixing system of FIG. 1 according to various embodiments described herein.

DETAILED DESCRIPTION

Figure 1:
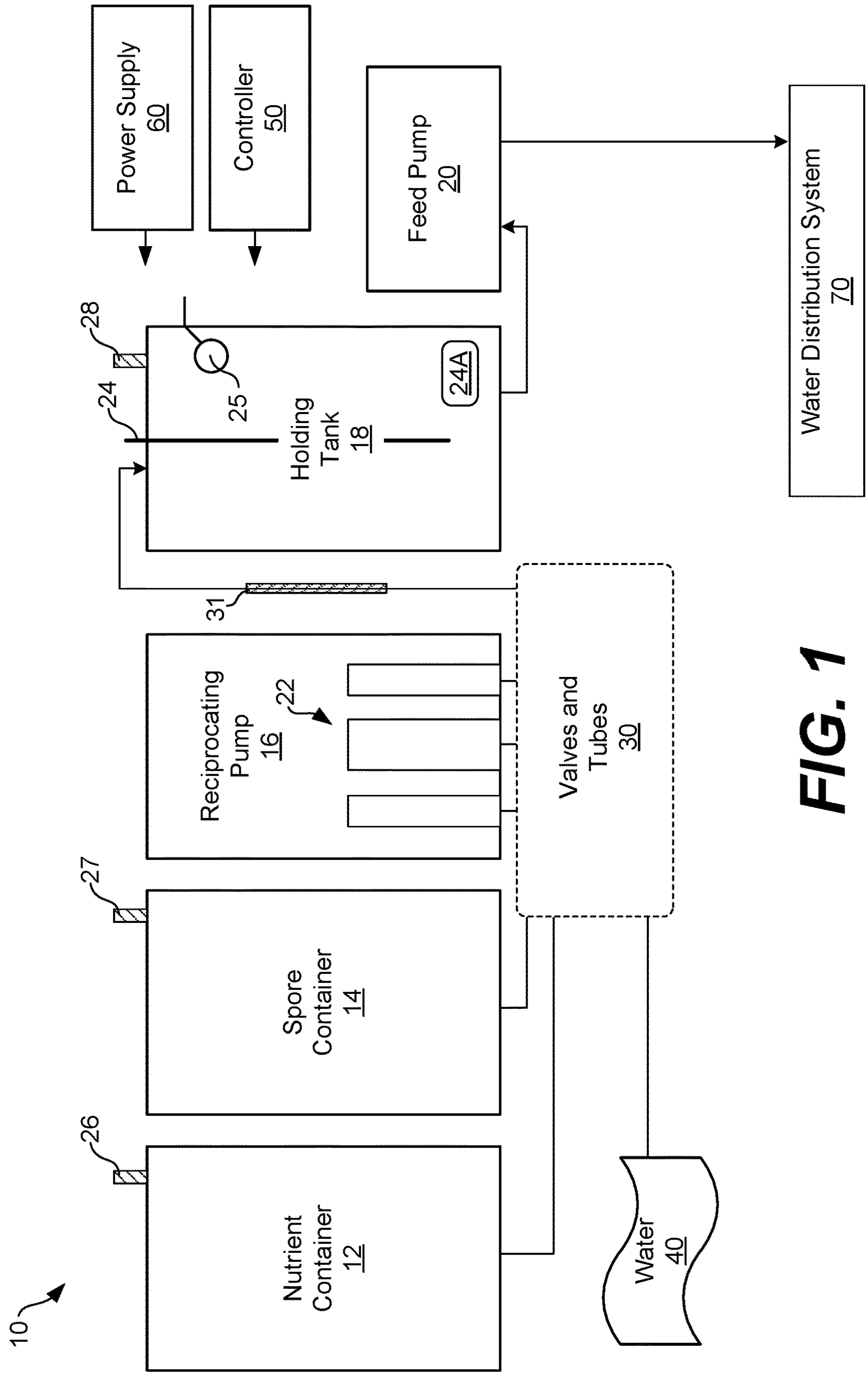
FIG. 1 illustrates an example metastable state spore incubation mixing system according to various embodiments described herein.

As noted above, germination is a process in which an organism grows, often out from a structure similar to a seed. In that context, spore germination is a process where spores effectively wake-up or are revived from a dormant state to a vegetative growth state. The first step in this process is one by which spores are activated and are induced to germinate, typically by an environmental signal called a germinant. This signal can be a nutrient such as an L-amino acid, among other types of nutrients. Nutrient germinants bind to receptors in the inner-membrane of the spore to initiate germination. Additionally, sugars have been shown to increase the binding affinity of L-amino acids for their cognate receptors.

The germinant signal initiates a cascade of events for the spore, such as the release of certain acids, the absorption of water, and an outgrowth stage including the initiation of the metabolic, biosynthetic, and deoxyribonucleic acid (DNA) replication and repair pathways. A ripening period occurs during the outgrowth stage in which molecular machinery (e.g., transcription factors, translation machinery, biosynthesis machinery, etc.) is activated but no morphological changes (e.g., such as cell growth) occur. The ripening period can vary in length based on the resources packaged with the spore during the process of sporulation. For example, malate is the preferred carbon source of several *Bacillus* species and spores typically contain a pool of malate that is used during the revival process. After the outgrowth step, spore revival is complete and cells are considered to be vegetatively growing. Between the dormant and vegetative growth states in the germination process, spores progress through a type of metastable state in which the spores are no longer dormant but also not yet in the vegetative growth phase. The addition of heat (e.g. 42° C.) is known to accelerate the process of germination, including the transition into the metastable state.

The embodiments described herein are directed to various aspects of metastable state spore incubation mixing systems. An example system includes a spore container to store spores, a nutrient container to store nutrients for the spores, an arrangement of valves and tubes, a reciprocating pump, a mixing tube, and a holding tank. In a drawing phase of the system, a controller can control the reciprocating pump or other pumping mechanism to draw a ratioed volume of the spores, the nutrients, and water through the valves and tubes. During an expelling phase of the system, the controller can control flow control valves to direct the spores, nutrients, and water through the mixing tube and into the holding tank. During a flushing phase, the controller can flow water through the mixing tube and other valves and tubes, to clear them of the mixture of spores and nutrients. Once the mixture is expelled and flushed into the holding tank, the controller can also direct a heater to heat the mixture in the holding tank. The mixture can be heated, in various cases, at a predetermined rate, over a predetermined period of time, and to a predetermined temperature. Once the mixture reaches the target temperature, the controller can also direct the system through a number of other phases of operation, including cooling and purging phases. Due to the heat and the nutrients, the spores in the mixture progress through germination to a type of metastable state in which most of the spores are neither dormant nor in the vegetative growth phase. From that state, the mixture can be mixed into the drinking water of animals (or plants) to facilitate digestion according to one example. In that context, the controller can control the rate and amount of the mixture provided to a water distribution system for animals, depending upon the type of animal drinking from it.

Turning to the drawings, FIG. 1 illustrates an example metastable state spore incubation mixing system 10 ("system 10") according to various embodiments described herein. In FIG. 1, the system 10 is representative of the types of components that can be used for metastable state spore incubation mixing. The parts or components are not drawn to scale in FIG. 1. The arrangement of the parts or components is not intended to be limiting, as other arrangements consistent with the concepts described herein are within the scope of the embodiments. Further, the parts or components shown in FIG. 1 are not exhaustive. In other words, the system 10 can include other components. Similarly, certain components shown in FIG. 1 can be omitted in certain cases. A more particular example of a system based on the concepts of the system 10 is described below with reference to FIG. 3. The system 10 can be an on-site system, being located and installed at the point of delivery to animals, plants, etc.

As shown, the system 10 includes a nutrient container 12, a spore container 14, a reciprocating pump 16, a holding tank 18, and a feed pump 20. Among other components, the system 10 also includes an arrangement of valves and tubes 30, a water supply 40, a controller 50, a power supply 60, and a water distribution system 70. The reciprocating pump 16 can include a number of pump barrels 22, and the holding tank 18 can include a heater 24, a thermocouple 24A, and a float switch 25. The float switch can be replaced with other methods commonly used to control water level such as flow sensors, water meters, etc. Further, in some cases, one or more of the nutrient container 12, the spore container 14, and the holding tank 18 can include vent filters 26-28, respectively. Additionally, the valves and tubes 30 can include a mixing tube 31.

The nutrient container 12 can be used to store a solution of nutrients, and the spore container 14 can be used to store a solution of spores. The solution of nutrients can preferably be embodied as any of the nutrient formulations described in U.S. patent application No. 62/318,587, U.S. patent publication number 2007/0281696, PCT application PCT/US17/26122, WIPO publication number 2017/176872, or U.S. patent application 62/567,974, which are incorporated by reference in their entireties, although the use of other formulations (even without nutrients) are within the scope of the embodiments. Further, the solution of spores can preferably be embodied as any of the spore formulations described in U.S. patent application No. 62/318,587, U.S. patent publication number 2007/0281696, PCT application PCT/US17/26122, WIPO publication number 2017/176872, or U.S. patent application 62/567,974, although the use of other formulations (even without nutrient spores) are within the scope of the embodiments. Thus, the system 10 is not limited to use with any particular solutions or formulations of nutrients or spores, although one use case does include the use of the formulations described in U.S. patent application No. 62/318,587, U.S. patent publication number 2007/0281696, PCT application PCT/US17/26122, or WIPO publication number 2017/176872.

The nutrient container 12 and the spore container 14 can be embodied as rigid, semi-rigid, or flexible containers formed from any suitable material or materials. If formed from a rigid or semi-rigid material, the nutrient container 12 and the spore container 14 can rely upon the vent filters 26 and 27 to pass air into the containers as the nutrients and the spores are drawn out of them by the reciprocating pump 16, thus relieving any positive or negative pressure in the containers. The vent filters 26 and 27 can thus include filters or membranes to remove particles from the air. In that way, the vent filters 26 and 27 can keep the contents of the nutrient container 12 and the spore container 14 from being contaminated with foreign particles and substances. A particular example of the nutrient container 12 and the spore container 14 is described below with reference to FIGS. 4A and 4B. If the nutrient container 12 and the spore container 14 are formed from flexible materials, such as plastic bags, the vent filters 26 and 27 can be omitted, as the bags can collapse without any need to allow air to pass air into the containers.

The reciprocating pump 16 relies upon the pump barrels 22 to draw the nutrients from the nutrient container 12, the spores from the spore container 14, and water from the water supply 40. Based on the supply of power and/or control signals from the controller 50, the nutrients, spores, and water can be respectively drawn by the reciprocating pump 16 from the nutrient container 12, the spore container 14, and the water supply 40, through the valves and tubes 30, and into respective barrels of the pump barrels 22. During this drawing phase of the system 10, the controller 50 can control (e.g., open and/or close) one or more valves among the valves and tubes 30 to direct the flow of the nutrients, spores, and water into the reciprocating pump 16. The pump barrels 22 in the reciprocating pump 16 can include one barrel for each of the spores, the nutrients, and the water, where each barrel is formed to hold a respective volume. In that case, when the reciprocating pump 16 draws the nutrients, the spores, and the water, it can draw them in a predetermined, ratioed volume. In one embodiment, the nutrients and spores do not mix together (or mix with the water) in the arrangement of the valves and tubes 30 between the nutrient container 12, the spore container 14, and the reciprocating pump 16. A particular example of the reciprocating pump 16 is described below with reference to FIGS. 6A and 6B.

The arrangement of the valves and tubes 30 can include a number of check valves, solenoid valves, tubes, connectors, etc. to route the nutrients, the spores, and the water between the containers, pumps, and tanks in the system 10. The nutrients, spores, and water can be routed through various paths in the valves and tubes 30, in part, by opening and closing solenoid valves in a particular pattern in multiple phases based on control signals provided by the controller 50 as described in further detail below. The tubes can be flexible or rigid tubes formed from any suitable material or materials. The valves and tubes 30 can be designed to form a closed system along with the other components in the system 10. An example arrangement of the valves and tubes 30, and the manner in which fluids can be routed through the valves and tubes 30 during various phases of the system 10, is described below with reference to FIGS. 2A-2J.

After the reciprocating pump 16 draws the nutrients, the spores, and the water into the pump barrels 22, the controller 50 can direct the reciprocating pump 16 to expel them back into the valves and tubes 30 during an expelling phase of the system 10. Although, the nutrients, spores, and water do not mix together in the valves and tubes 30 when being drawn into the reciprocating pump 16, the nutrients, spores, and water can mix together when being expelled from the reciprocating pump 16 and pushed to the holding tank 18. This mixing can be facilitated by the mixing tube 31, which is in fluid communication between the reciprocating pump 16 and the holding tank 18. A particular example of the mixing tube 31 is described below with reference to FIG. 5. In a flushing phase, the controller 50 can flush water from the water supply 40 through the mixing tube 31 to clear it from the mixture of the nutrients and spores. In the flushing phase, the majority of the mixture is cleared from the mixing tube 31 and into the holding tank 18.

The holding tank 18 can hold the mixture of the nutrients, spores, and water. The holding tank 18 can be formed from any suitable material or materials, such as plastics, glass, or stainless steel. The holding tank 18 can also be used to heat the mixture of the nutrients, spores, and water using the heater 24, which can be positioned inside the holding tank 18, wrapped around, or integrated with the holding tank 18. A certain level or volume of fluid in the holding tank 18 can be detected by the float switch 25. A particular example of the holding tank 18 is described below with reference to FIGS. 7A and 7B.

Once the mixture is pumped into the holding tank 18 using the reciprocating pump 16, the controller 50 can direct the heater 24 to heat the mixture in a heating phase of the system 10. The controller 50 can direct the heater 24 to heat the mixture to a predetermined temperature and, possibly, heat the mixture to the predetermined temperature within or during a predetermined time. In some cases, the heater 24 can heat the mixture in the holding tank 18 while the reciprocating pump 16 performs multiple drawing and expelling phases. With the mixture of the nutrients and the spores and the application of heat from the heater 24, the germination process of the spores is initiated within the holding tank 18.

Based on test results, the predetermined temperature can be about 42° Celsius to transition a significant number (e.g., about 95%) of the spores into the metastable state between the dormant and vegetative growth states, although other temperatures above or below 42° Celsius can be targeted. In one embodiment, the controller 50 can direct the heater 24 to heat the mixture to 42° Celsius relatively quickly, but preferably not less than about 2 minutes. In other cases, the controller 50 can direct the heater 24 to heat the mixture to a temperature of less than 42° Celsius during a relatively longer period of time (i.e., longer than 2 minutes), or heat the mixture to a temperature of greater than 42° Celsius during a relatively shorter period of time (i.e., less than 2 minutes). Overall, the controller 50 can be designed to monitor the conditions within the holding tank 18, including the volume of water, the temperature, and other relevant factors, to approach and maintain conditions suitable for germination of the spores and to transition a significant number (e.g., about 95% or more) of the spores into the metastable state. During the heating phase, the controller 50 can monitor the temperature of the mixture in the holding tank 18 using the thermocouple 24A and, when the mixture reaches a predetermined temperature, transition the system 10 to a cooling phase.

In an effort to maintain the spores in the metastable state (and slow them from reaching the vegetative growth state), the controller 50 can flush unheated water through the valves and tubes 30 and into the holding tank 18 in a cooling phase of the system 10. To that end, the controller 50 can control the valves and tubes 30 to supply the water from the water supply 40 to the holding tank 18 in the cooling phase. The controller 50 can transition the system 10 to the cooling phase when it detects that the temperature of the mixture in the holding tank 18 reaches the predetermined temperature, after the mixture reaches the predetermined temperature for a certain period of time, or at other suitable times. In one example, the controller 50 can flush water into the holding tank 18 during the cooling phase until the float switch 25 indicates that the level of fluid in the holding tank 18 reaches a certain level. At that point, the controller 50 can transition the system 10 to a purging phase.

The system 10 aims to deliver spores for ingestion by animals, where the spores are alive and reach the vegetative growth state within the gut of the animals after being ingested. Thus, the system 10 seeks to maintain the spores in the metastable state (and slow them from reaching the vegetative growth state) because testing has shown that spores in the metastable state stand a better chance of living through the later phases of the system 10, including the purging phase described below, and also live through being mixed with more water from the water supply 40, which may contain chlorine, in the water distribution system 70.

During a purging phase of the system 10, the controller 50 can control the feed pump 20 to draw the mixture out of the holding tank 18 at a rate for mixing with water from the water supply 40. The feed pump 20 can be embodied as a peristaltic pump in one embodiment, although other types of pumps can be used. A peristaltic pump may be preferable so that no parts of the feed pump 20 (other than the flexible pump tube) come into contact with the mixture from the holding tank 18. Additionally, peristaltic pumps offer relatively low levels of shear forces, making them preferable for handling the spores with out damaging them, and the speed of peristaltic pumps can be easily and accurately controlled. The vent 28 displaces the air or fluid in the in the holding tank 18. The vent 28 also can be used as an overflow if too much water was added to the holding tank 18. The vent 28 can include a filter to remove particles from the air. During the purging phase, the vent filter 28 can remove particles from the air being drawn into the holding tank 18. In that way, the vent filter 28 can keep the internal contents of the holding tank 18 from being contaminated with foreign particles and substances.

During and/or after the purging phase, the controller 50 can also control the valves and tubes 30 to supply water from the water supply 40 to the holding tank 18. In that way, the mixture in the holding tank 18 can be diluted during the purging phase of the system 10. Additionally or alternatively, the holding tank 18 can be rinsed with the water to clear it from the spores.

As shown in FIG. 1, the output of the feed pump 20 is mixed with water from the water supply 40 before being provided to the water distribution system 70. The water distribution system 70 can be embodied as a system for the distribution of water for ingestion by one or more animals. By controlling the pump or feed rate of the feed pump 20, the controller 50 can control, at least to some extent, the concentration of the mixture from the holding tank 18 in the water from the water supply 40, as the combination of them is provided to the water distribution system 70. Thus, the controller 50 can control the amount of the mixture provided to the water distribution system 70 depending upon the type and number of animal(s) drinking from it and other relevant factors. The controller 50 can also control timing to provide mixture at the appropriate time of day (e.g. based on activity, sun light, sun rise, water use, etc.)

The controller 50 can be embodied as analog, digital, or mixed analog and digital processing circuitry, including memory, and associated software configured to control the operation of the system 10. The controller 50 can be embodied as an embedded real-time system, such as a programmable logic controller (PLC), which produces time-sensitive control signals for and receives feedback signals from other components of the system 10 during operation. The controller 50 can include one or more memory devices to store computer-readable instructions that, when executed by processing circuitry of the controller 50, directs the controller 50 to control various aspects of the operation of the system 10. Thus, the controller 50 can direct the system 10 through multiple phases of operation as described herein.

The power supply 60 can be embodied as any suitable power supply for the components of the system 10. As one example, the power supply 60 can include an AC/DC linear or switching power converter, although any suitable power supply can be relied upon.

Figure 2A:
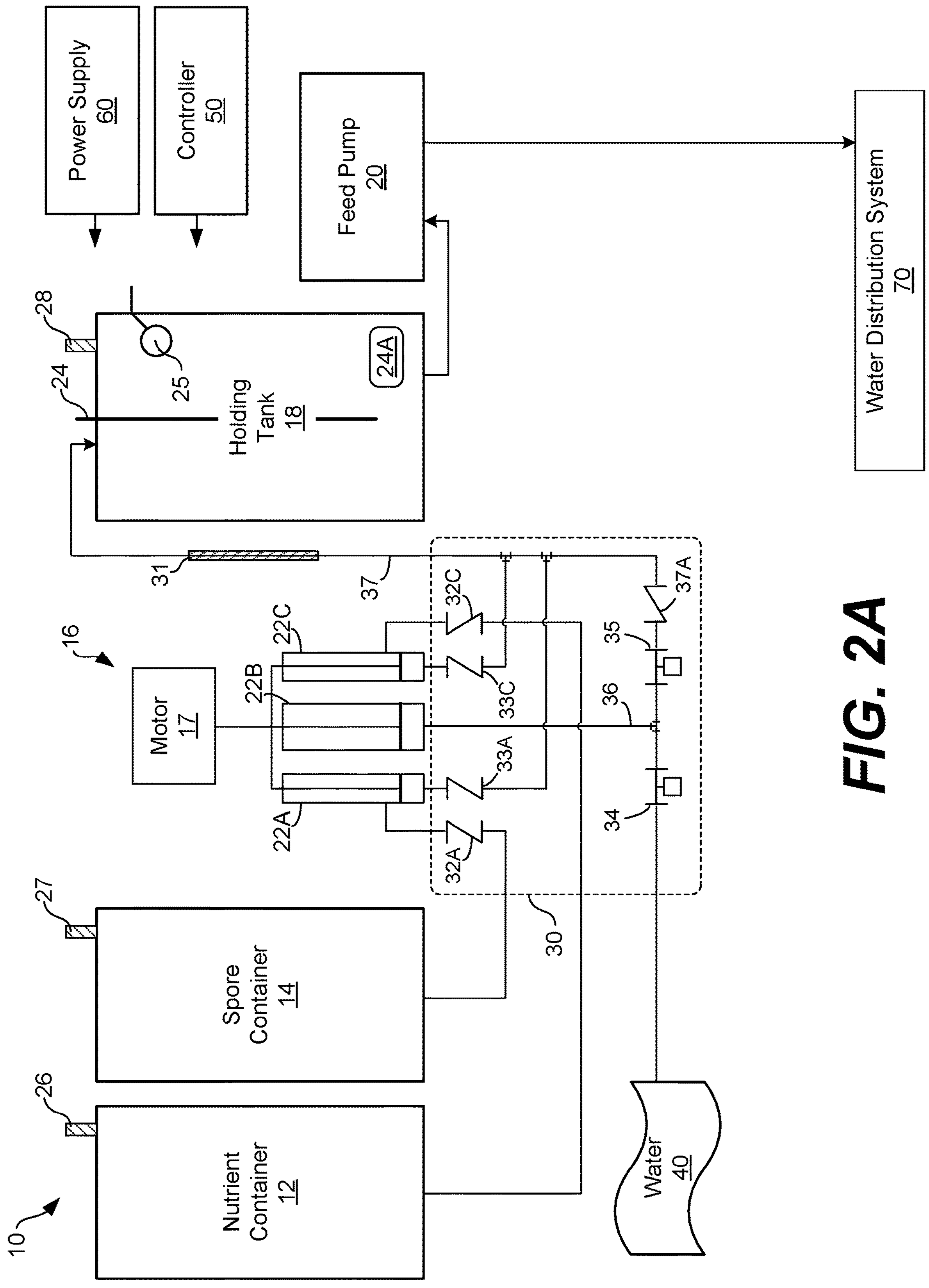
FIG. 2A further illustrates the metastable state spore incubation mixing system shown in FIG. 1 according to various embodiments described herein.

FIG. 2A further illustrates the system 10 shown in FIG. 1. In FIG. 2, an example arrangement of the valves and tubes 30 is expanded in greater detail. Among other components, the valves and tubes 30 include a number of check valves 32A, 33A, 32C, 33C, 37A, etc., a number of solenoid valves 34 and 35, a water pathway 36, and a mixing pathway 37 including the mixing tube 31. The check valves, solenoid valves, and tubes can be embodied as any suitable valves and tubes for the application and concepts described herein. The arrangement of the valves and tubes 30 is not intended to be limiting as other arrangements consistent with the concepts described herein can be relied upon. Further, as shown, the barrels 22 of the reciprocating pump 16 include a spore barrel 22A, a water barrel 22B, and a nutrient barrel 22C. The barrels 22A-22C can each hold a different volume of fluid as described in further detail below.

The check valve 32A is placed inline in a tube that creates a closed fluid pathway between the spore container 14 and the spore barrel 22A of the reciprocating pump 16. The check valve 33A is placed inline in a tube that creates a closed fluid pathway between the spore barrel 22A and the mixing pathway 37. The check valve 32A permits the spores to flow from the spore container 14 to the spore barrel 22A during the drawing phase of the reciprocating pump 16 but prevents reverse flow during the expelling phase, and the check valve 33A permits the spores to flow from the spore barrel 22A to the mixing pathway 17 during the expelling phase but prevents reverse flow during the drawing phase.

The check valve 32C is placed inline in a tube that creates a closed fluid pathway between the nutrient container 12 and the nutrient barrel 22C of the reciprocating pump 16. The check valve 33C is placed inline in a tube that creates a closed fluid pathway between the nutrient barrel 22C and the mixing pathway 37. The check valve 32C permits the nutrients to flow from the nutrient container 12 to the nutrient barrel 22C during the drawing phase of the reciprocating pump 16 but prevents reverse flow during the expelling phase, and the check valve 33C permits the nutrients to flow from the nutrient barrel 22C to the mixing pathway 17 during the expelling phase but prevents reverse flow during the drawing phase. The check valves may also be built in or on the bottles or pumps.

The solenoid valves 34 and 35 are placed inline in the mixing pathway 37, and the controller 50 can control (e.g., open and/or close) the solenoid valves 34 and 35 to direct the flow of water from the water supply 40 among multiple paths in the system 10. For example, the controller 50 can control (e.g., open and/or close) the solenoid valves 34 and 35 to prevent water from flowing into the system 10, to direct water into the water pathway 36, and to direct water into the water barrel 22B of the reciprocating pump 16. The controller 50 can control the solenoid valves 34 and 35 to direct the water through those different paths at different phases in the operation of the system 10 as described below with reference to FIGS. 2B-2J.

As described herein, the controller 50 directs the system through multiple phases of operation. As an example, the controller 50 can sequence the system through drawing, expelling, flushing, heating, cooling, purging, and rinsing phases of operation, among others. The controller 50 is configured to open and/or close one or both of the solenoid valves 34 and 35 at certain times (or at certain timings) to transition the system 10 through the different phases. Additionally, the controller 50 is configured to control the heater 24 and the feed pump 20 at certain times (or at certain timings) to transition the system 10 through the different phases.

Figure 2B:
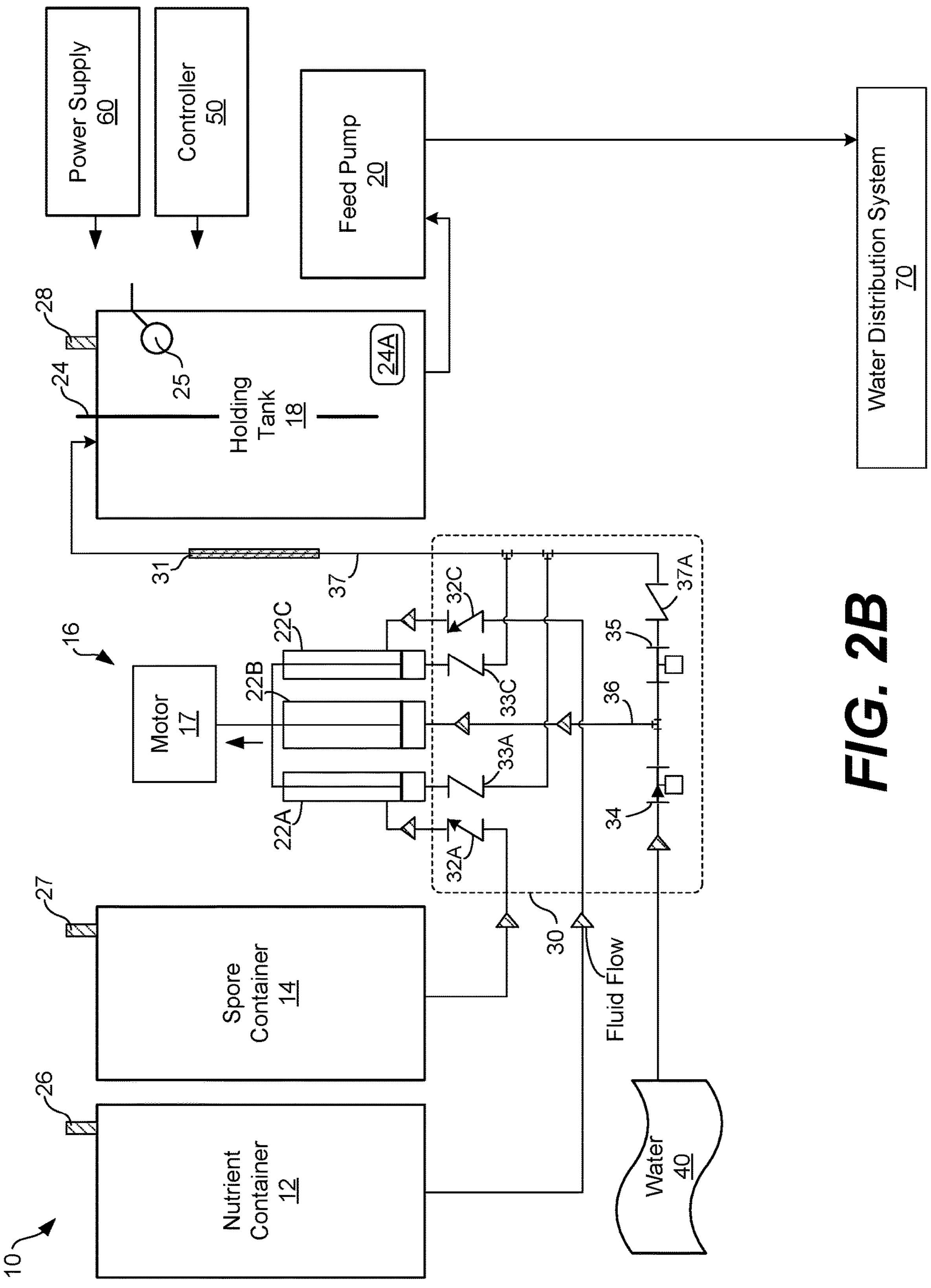
FIG. 2B illustrates a drawing phase of the mixing system shown in FIG. 1 according to various embodiments described herein.

To start, FIG. 2B illustrates the drawing phase of the mixing system 10. In the drawing phase, the controller 50 is configured to open the solenoid valve 34 and to close the solenoid valve 35 as shown. In that case, water from the water supply 40 can flow through the water pathway 36. The controller 50 is also configured to control the reciprocating pump 16 to simultaneously draw the spores from the spore container 14 to the spore barrel 22A, draw the nutrients from the nutrient container 12 to the nutrient barrel 22C, and draw the water through the water pathway 36 to the water barrel 22B. As described in further detail below with reference to FIGS. 6A and 6B, the reciprocating pump 16 can include a motor 17 to simultaneously move or pull plungers associated with the barrels 22A-22C in an upward direction to draw the spores, water, and nutrients. When the reciprocating pump 16 moves or pulls the plungers up, the movement draws the spores, water, and nutrients into the barrels 22A-22C, respectively, in a predetermined, ratioed volume. In this drawing phase, the check valves 32A and 32C can open with fluid flowing through them, but the check valves 33A and 33C are closed as shown.

Figure 2C:
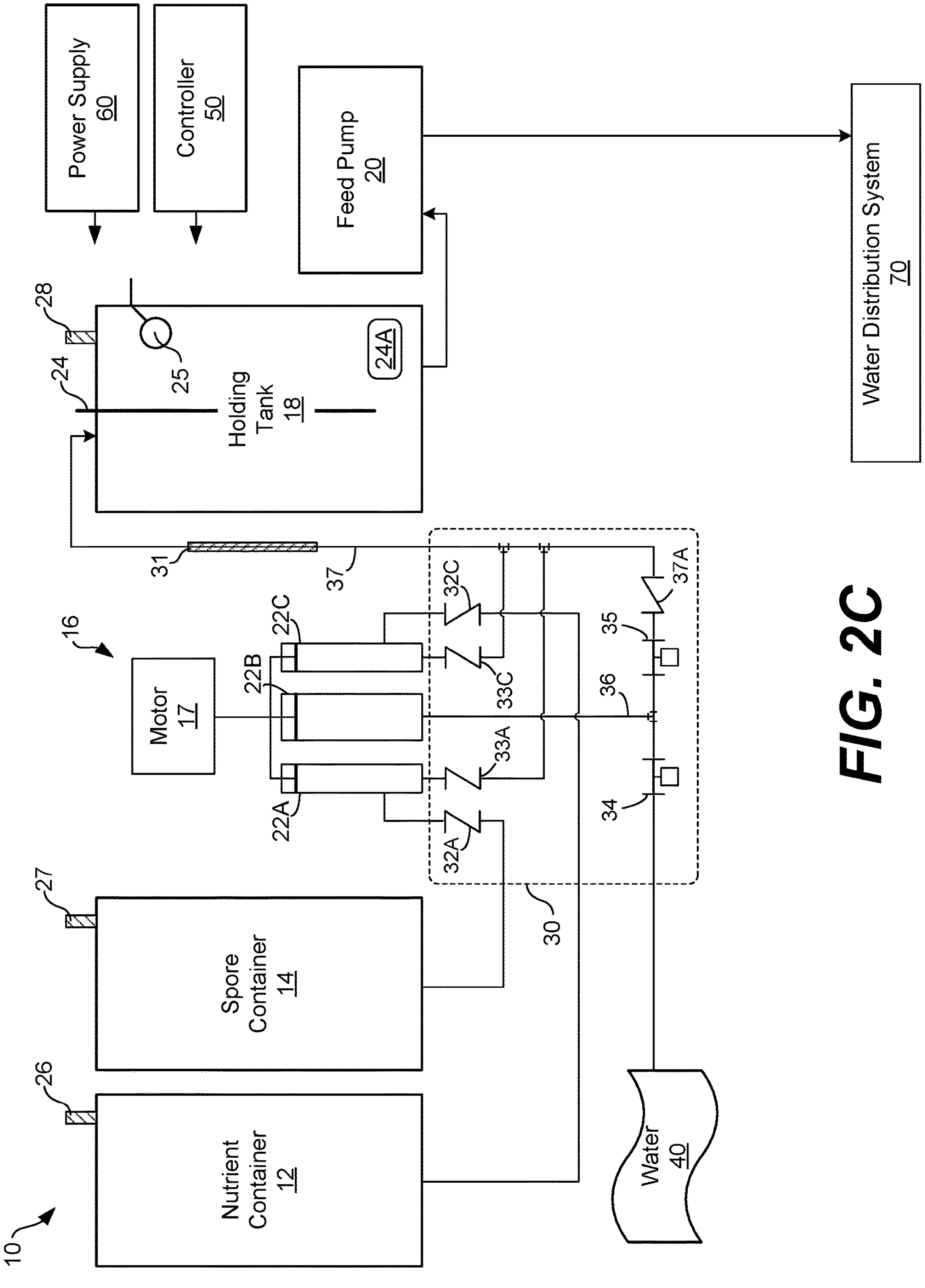
FIG. 2C illustrates an end of the drawing phase of the mixing system shown in FIG. 1 according to various embodiments described herein.

FIG. 2C illustrates an end of the drawing phase of the mixing system 10. At this point, the reciprocating pump 16 has pulled the plungers to the top of the barrels 22A-22C as shown. Further, the spore barrel 22A is filled with spores, the water barrel 22B is filled with water, and the nutrient barrel 22C is filled with nutrients. The controller 50 can now close the solenoid valve 34, and the check valves 32A and 32C also close.

Figure 2D:
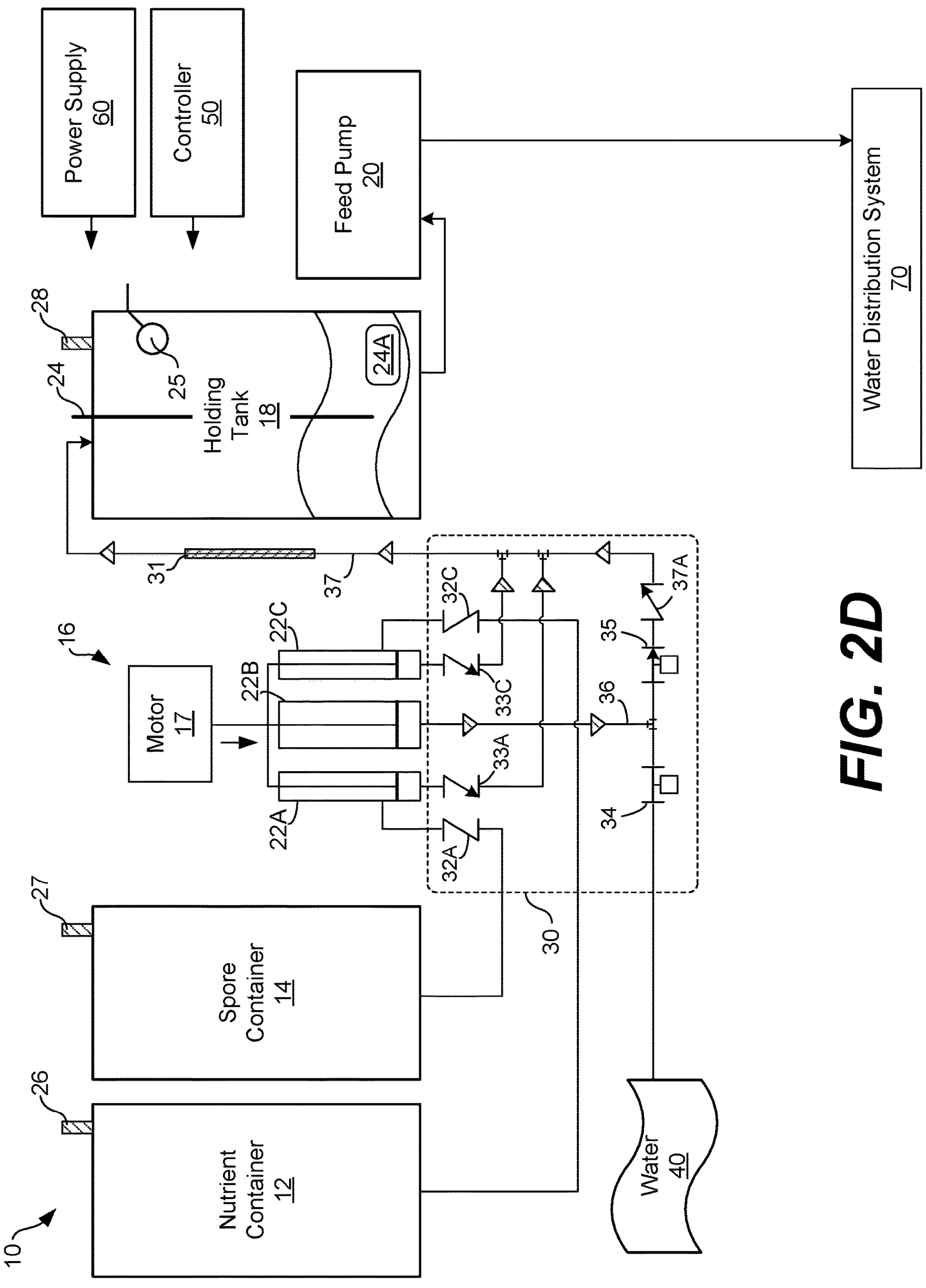
FIG. 2D illustrates an expelling phase of the mixing system shown in FIG. 1 according to various embodiments described herein.

FIG. 2D illustrates an expelling phase of the mixing system 10. In the expelling phase, the controller 50 is configured to close the solenoid valve 34 and to open the solenoid valve 35. The controller 50 is also configured to control the reciprocating pump 16 to push the plungers down, and that movement expels the spores, water, and nutrients out of the barrels 22A-22C. Thus, the spores are expelled from the spore barrel 22A to the mixing pathway 37, and the nutrients are expelled from the nutrient barrel 22C to the mixing pathway 37. Further, the water is expelled from the water barrel 22C, through the solenoid valve 35, through the check valve 37A, and to the mixing pathway 37. In the expelling phase, the check valves 33A, 33C, and 37A can open with fluid flowing through them, but the check valves 32A and 32C are closed as shown.

The spores, water, and nutrients can mix together in the mixing pathway 37, and that mixture is provided to the holding tank 18. This mixing can be facilitated by the mixing tube 31, which is inline in the mixing pathway 37 to the holding tank 18. A particular example of the mixing tube 31 is described below with reference to FIG. 5. To a large extent, the mixture of the spores, water, and nutrients are pushed from the reciprocating pump 16 into the holding tank 18 during the expelling phase, except for the remainder of the mixture left in the mixing pathway 37 and the mixing tube 31.

In some cases, the controller 50 can direct the system 10 to perform the drawing and expelling phases multiple times to fill the holding tank 18 to a certain level. For example, the controller 50 can direct the system 10 to perform the drawing and expelling phases three or more times, consecutively, before turning to the flushing and heating phases described below.

Figure 2E:
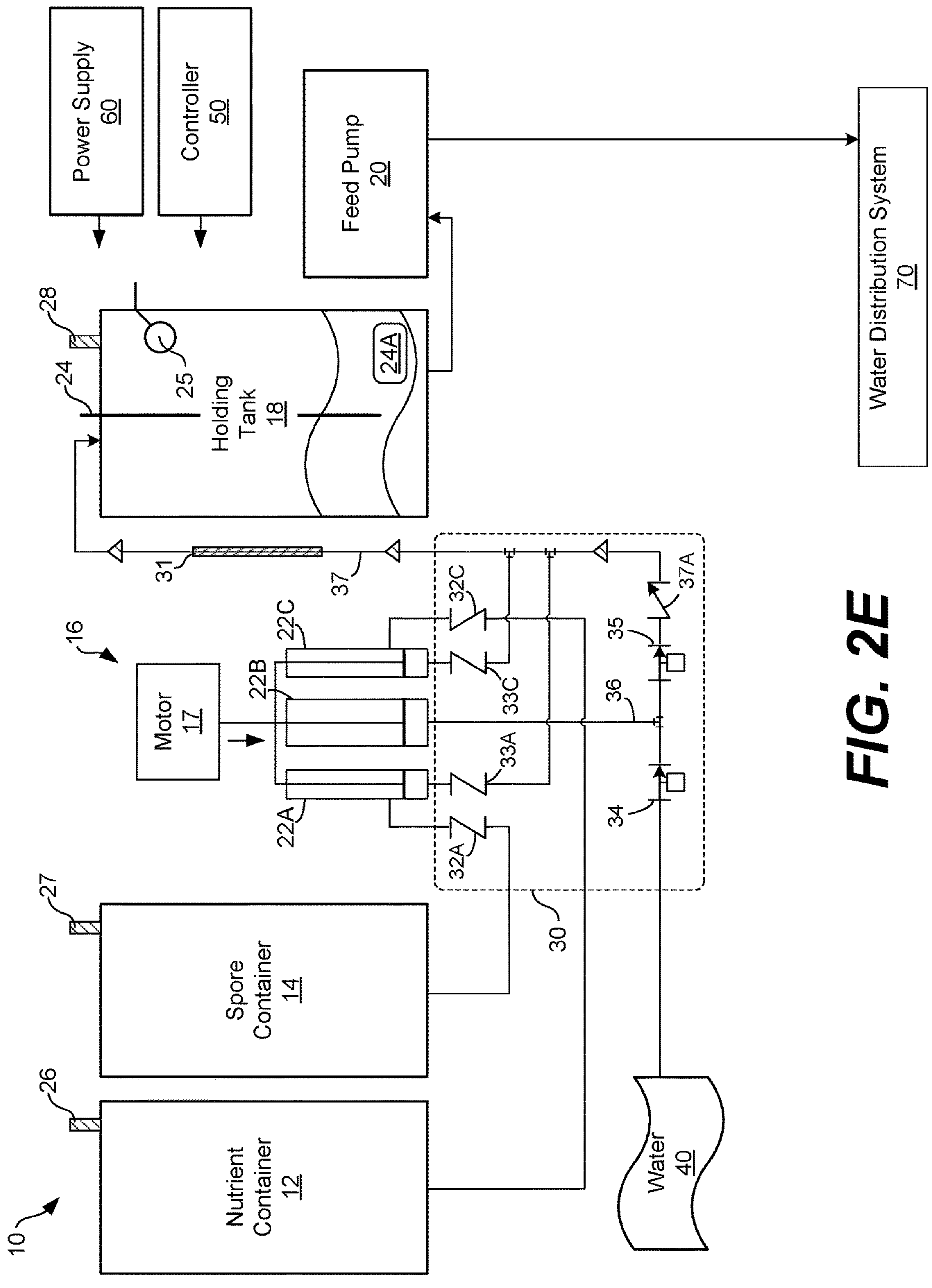
FIG. 2E illustrates a flushing phase of the mixing system shown in FIG. 1 according to various embodiments described herein.

FIG. 2E illustrates a flushing phase of the mixing system 10. In the flushing phase, the controller 50 may be configured to open both the solenoid valve 34 and the solenoid valve 35. The check valve 37A is also open. As can be appreciated, similar functionality can be achieved with a single solenoid as well as a three-way solenoid, and other types of shut off valves can also be used. In this phase, the controller 50 can flush water from the water supply 40 through the mixing pathway 37 and the mixing tube 31 to clear the mixing pathway 37 from the mixture of the spores and nutrients. In the flushing phase, the mixture is fully cleared from the mixing pathway 37 and the mixing tube 31 and into the holding tank 18. The controller 50 may open both the solenoid valve 34 and the solenoid valve 35 for a relatively short period of time, such as just long enough to clear the relatively small volume of the mixing pathway 37 and the mixing tube 31.

Figure 2F:
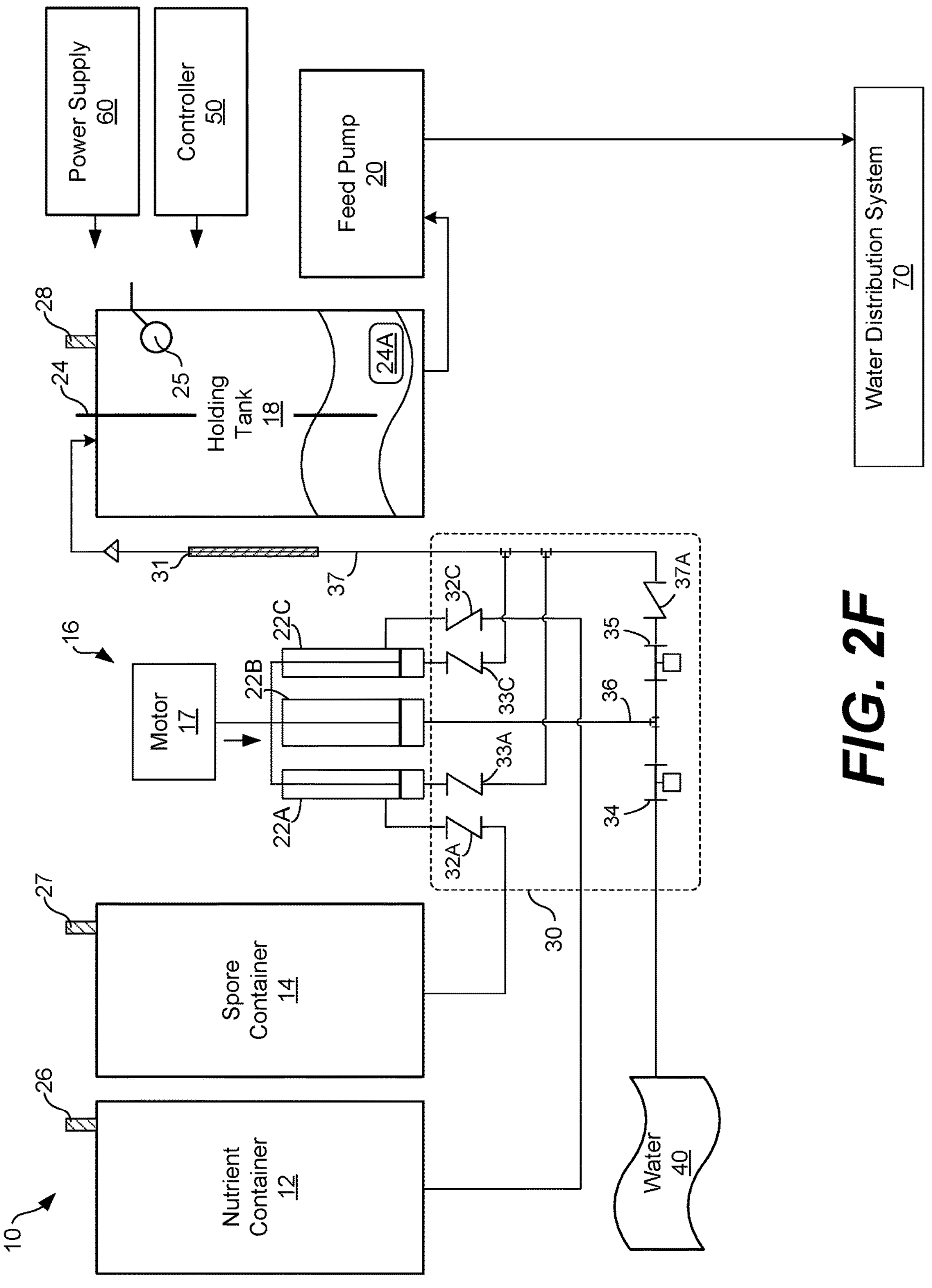
FIG. 2F illustrates a heating phase of the mixing system shown in FIG. 1 according to various embodiments described herein.

FIG. 2F illustrates a heating phase of the mixing system 10. In the heating phase, the controller 50 is configured to close both the solenoid valve 34 and the solenoid valve 35. Also, all the check valves are also closed. The controller 50 is also configured to direct the heater 24 to heat the mixture in the holding tank 18. As shown, the heater 24 extends into the holding tank 18 and contacts the mixture. In other cases, the heater 24 can heat the holding tank 18 with an outside heater (e.g. silicone pad) to heat the mixture. Additionally, the water can be heated in a separate holding tank before the water enters the barrel 22B of the reciprocating pump 16. With the mixture of the nutrients and the spores in the holding tank 18 and the application of the heat from the heater 24, the germination process of the spores is initiated within the holding tank 18.

During the heating phase, the controller 50 can monitor the temperature of the mixture in the holding tank 18 using the thermocouple 24A and, when the mixture reaches a predetermined temperature, transition the system 10 to a cooling phase. The predetermined temperature, in one example, is about 42° Celsius, although other temperatures can be targeted. As described herein, the controller 50 is designed to monitor the conditions within the holding tank 18, including the volume of water, the temperature, and other relevant factors, to achieve the types of conditions suitable for germination of the spores to the metastable state.

Figure 2G:
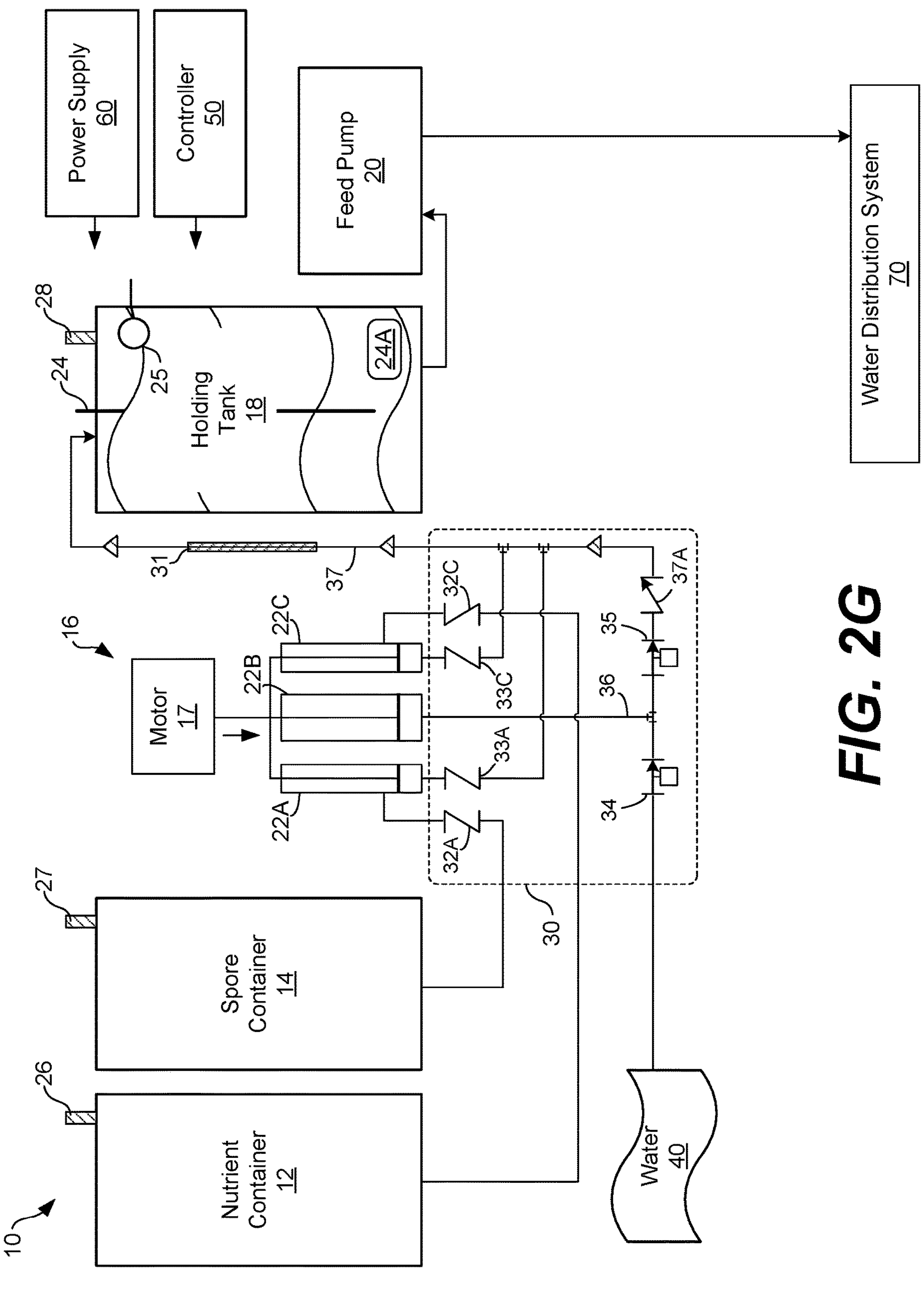
FIG. 2G illustrates a cooling phase of the mixing system shown in FIG. 1 according to various embodiments described herein.

FIG. 2G illustrates a cooling phase of the mixing system 10. In the cooling phase, the controller 50 is configured to open both the solenoid valve 34 and the solenoid valve 35. The check valve 37A is also open. Thus, the controller 50 can flush water from the water supply 40 into the holding tank 18 during the cooling phase. The controller 50 can transition the system 10 to the cooling phase when it detects that the temperature of the mixture in the holding tank 18 reaches the predetermined temperature for germination of the spores to the metastable state. In one example, the controller 50 can flush water into the holding tank 18 during the cooling phase until the float switch 25 indicates that the level of fluid in the holding tank 18 reaches a certain level. At that point, the controller 50 can transition the system 10 to a mixture purging phase.

Figure 2H:
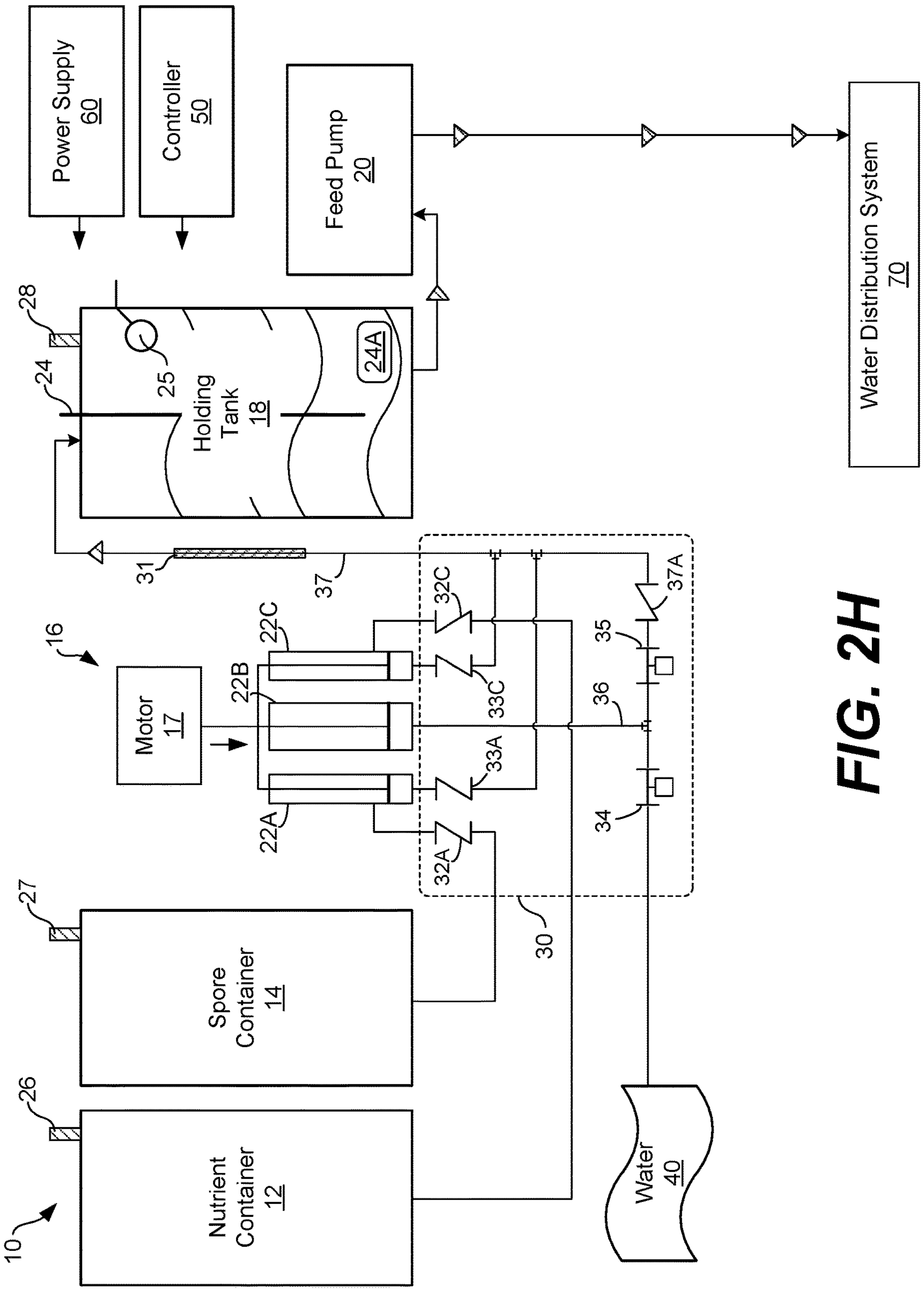
FIG. 2H illustrates a mixture purging phase of the mixing system shown in FIG. 1 according to various embodiments described herein.

FIG. 2H illustrates a mixture purging phase of the mixing system 10. In the mixture purging phase of the system 10, the controller 50 can close all solenoid and check valves and control the feed pump 20 to draw the mixture out of the holding tank 18. The mixture can be provided directly to the water distribution system 70 or mixed with water before being provided to the water distribution system 70. The water distribution system 70 can be an extension of the water supply 40, and it can also include systems for providing water to animals. The controller 50 can draw the mixture out from the holding tank 18 at any suitable rate. As one example, the controller 50 can draw the mixture at a certain rate for mixing with water from the water supply 40 as it is provided to the water distribution system 70, but it is not necessary that the mixture is further diluted with water. The water distribution system 70 can be the outlet connection point of the supply line (as shown in drawings).

A peristaltic pump may be preferable for the feed pump 20 so that no parts of the feed pump 20 come into contact with the mixture from the holding tank 18, although other types of pumps can be used. During the purging phase, a vent 28 can include a filter to remove particles from the air being drawn into the holding tank 18. Alternatively, the vent 28 may only allow for displacement of air and liquids in the holding tank 18. The vent 28 may have a filter to keep the internal contents of the holding tank 18 from being contaminated with foreign particles and substances.

After the purging phase, the controller 50 can also open both the solenoid valves 34 and 35 to supply water from the water supply 40 to the holding tank 18, similar to the way shown in FIG. 2G. In that way, any remaining mixture in the holding tank 18 can be rinsed out. This water can also be drawn out of the holding tank 18 using the feed pump 20 to empty it, similar to the way shown in FIG. 2H.

Figure 3:
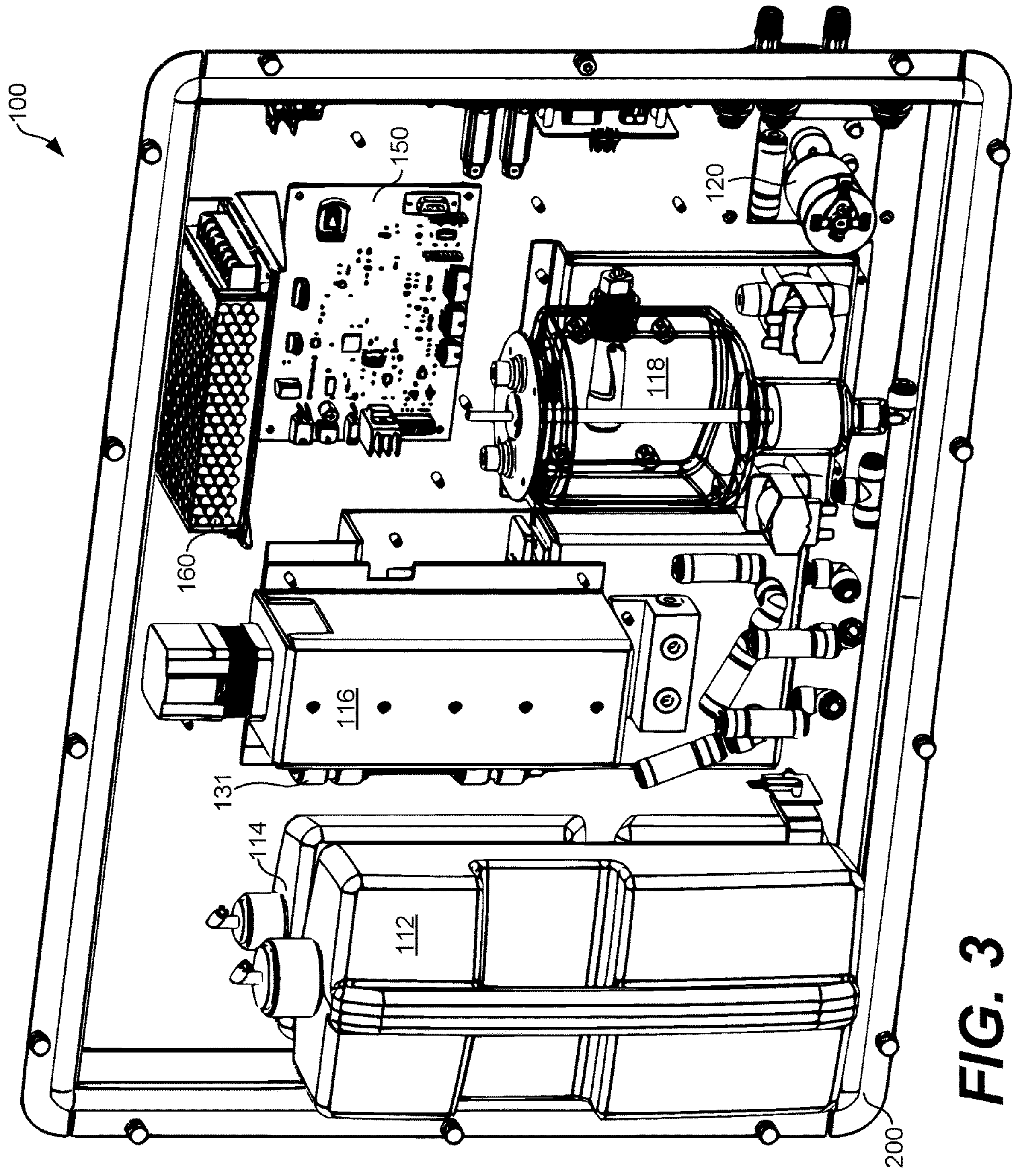
FIG. 3 illustrates an example embodiment of a metastable state spore incubation mixing system according to various embodiments described herein.

FIG. 3 illustrates an example embodiment of a metastable state spore incubation mixing system 100 ("system 100") according to various embodiments described herein. The system 100 is shown as a representative example and includes an arrangement of components analogous to those of the system 10 described above, although other arrangements can be used. Among other components, the system 100 includes a nutrient container 112, a spore container 114, a reciprocating pump 116, a holding tank 118, and a feed pump 120. The system 100 also includes an arrangement of valves and tubes (not individually shown), a mixing tube 131, a controller 150, and a power supply 160. For clarity in illustration, the tubes in the system 100 are omitted from view. The nutrient container 112 and the spore container 114 are shown in greater detail in FIGS. 4A and 4B, the mixing tube 131 is shown in greater detail in FIG. 5, the reciprocating pump 116 is shown in greater detail in FIGS. 6A and 6B, and the holding tank 118 is shown in greater detail in FIGS. 7A and 7B.

The components of the system 100 can be enclosed within an enclosure 200, which can include a front cover with an interface including a control panel with buttons and a display (not shown) to monitor and control the operations of the system 100. The feed pump 120 can be embodied as a peristaltic pump, although other types of pumps can be used. In one embodiment, the replaceable parts of the feed pump 120, such as the flexible pump tube, can be accessible outside of the enclosure 200, for maintenance purposes.

Figure 4A:
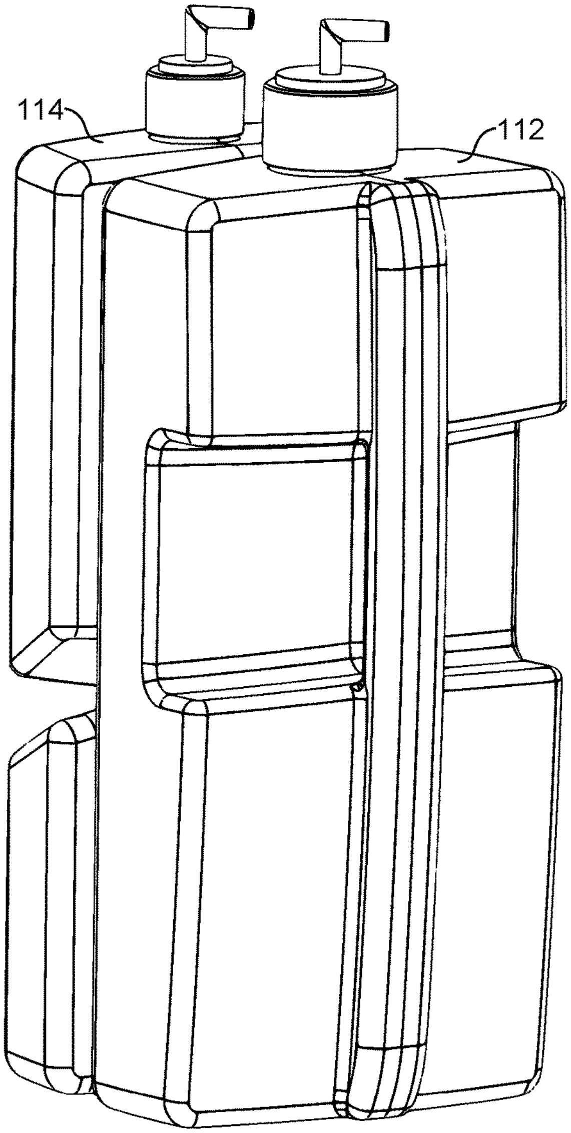
FIGS. 4A and 4B illustrate example spore and nutrient containers for the mixing system shown in FIG. 3 according to various embodiments described herein.
Figure 4B:
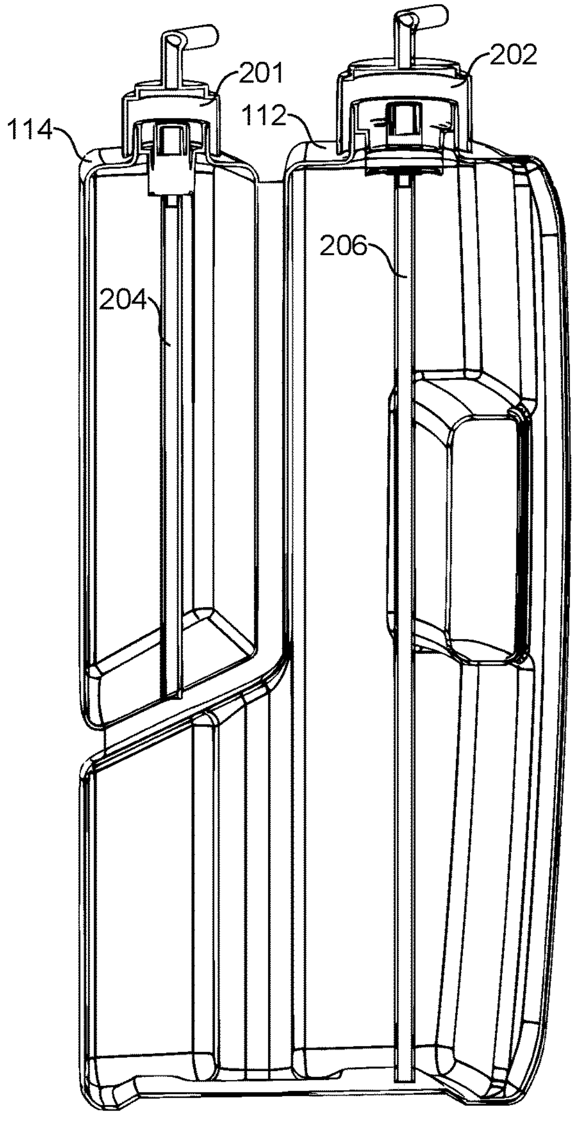

FIG. 4A illustrates the nutrient container 112 and the spore container 114 for the mixing system 100 shown in FIG. 3, and FIG. 4B illustrates a cross-sectional view of those containers. As shown, the nutrient container 112 and the spore container 114 are embodied as two-part semi-rigid containers formed from plastic materials. In other embodiments, the containers 112 and 114 can be formed from different materials, have different shapes, be formed at different sizes, etc.

The nutrient container 112 includes a vent cap 202 having a filter, as described herein, to allow air but prevent particles from entering the nutrient container 112 as the contents of the nutrient container 112 are drawn out through the straw 206. Similarly, the spore container 114 includes a vent cap 201 having a filter to allow air but prevent particles from entering the spore container 114 as the contents of the spore container 114 are drawn out through the straw 204.

The vent caps 201 and 202 fit into the necks of the nutrient container 112 and the spore container 114 and can serve as a type of containment lock to prevent the nutrients and the spores from spilling. When the nutrient container 112 and the spore container 114 are not in use, a spring-loaded valve in the vent caps 201 and 202 can be held closed and a breathable membrane or filter allows gasses to pass through it, relieving any positive or negative pressure in the containers. As one example, the vent caps 201 and 202 can be embodied as SafTflo® inserts manufactured by RD Industries, Inc. of Omaha, Nebr., although similar inserts, caps, and vents can be relied upon. In other embodiments, the bottle may be replaced with a sealed bag that may not require a vent or filter.

Figure 5:
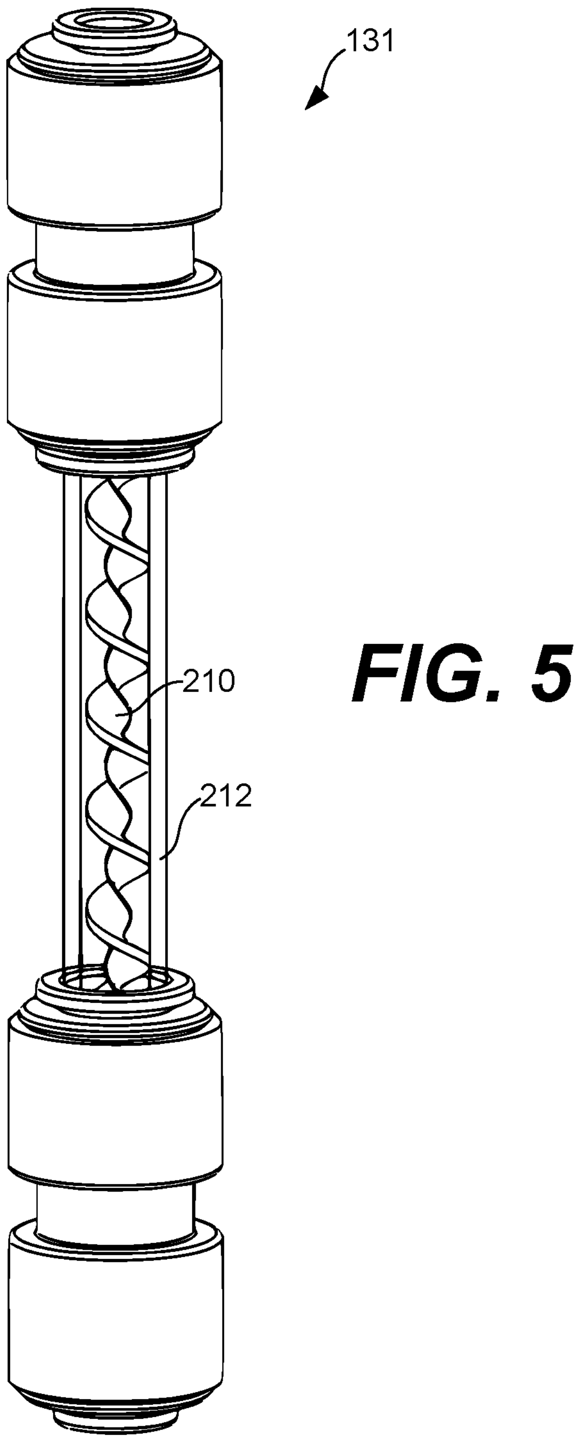
FIG. 5 illustrates an example mixing tube for the mixing system shown in FIG. 3 according to various embodiments described herein.

FIG. 5 illustrates an example of the mixing tube 131 shown in FIG. 3. In the system 100, the mixing tube 131 is placed in a closed fluid pathway between the reciprocating pump 116 and the holding tank 118. As shown, the mixing tube 131 includes a mixing spiral 210 within a length of tube 212. The mixing spiral 210 is formed to have helical twists alternating in right- and/or left-hand rotations. Thus, the mixing tube 131 can be relied upon to thoroughly mix the spores, nutrients, and water before that mixture flows into the holding tank 118. As can be appreciated, other devices may also be used to mix the solutions.

Figure 6A:
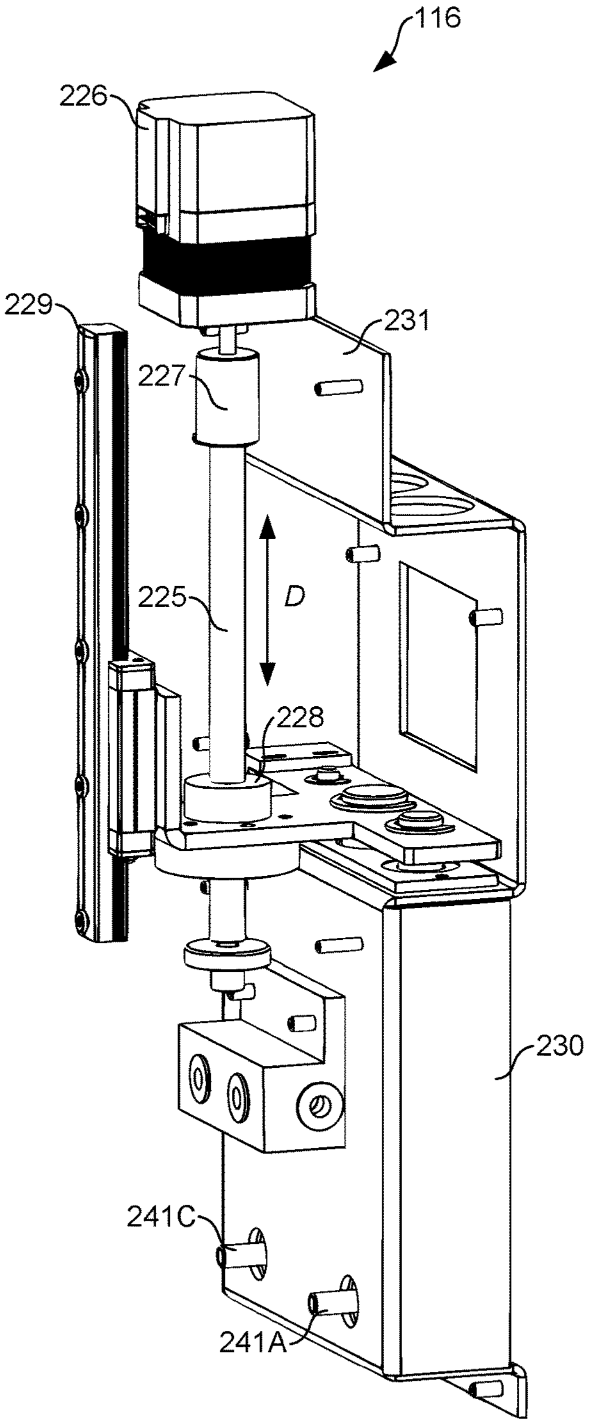
FIGS. 6A and 6B illustrate an example reciprocal pump for the mixing system shown in FIG. 3 according to various embodiments described herein.
Figure 6B:
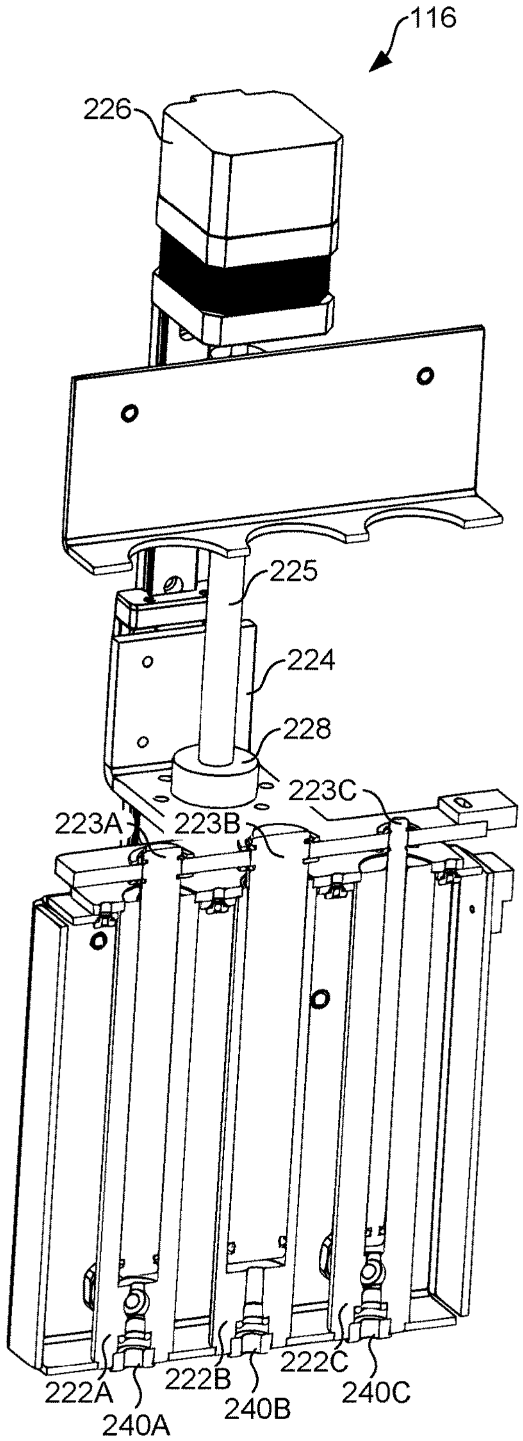

FIG. 6A illustrates an example of the reciprocal pump 116 for the system 100 shown in FIG. 3, and FIG. 6B illustrates a cross-sectional view of the reciprocal pump 116. The reciprocal pump 116 includes barrels 222A-222C, respectively, to hold nutrients, water, and spores and plungers 223A-223C, which fit within the barrels 222A-222C, respectively. The reciprocal pump 116 also includes a mounting bracket 224, and one end of each of the plungers 223A-223C is attached to the mounting bracket 224. The reciprocal pump 116 also includes a displacement rod 225, a motor 226, a motor coupling 227 between the displacement rod 225 and the motor 226, a displacement coupling 228 mounted through the mounting bracket 224, and a linear displacement bracket 229.

The barrels 222A-222C and the plungers 223A-223C can be formed from any suitable material, such as stainless steel or plastic. Each of the plungers 223A-223C can include a sealing ring, such as a rubber O-ring, at a distal end within a corresponding barrel 222A-222C. The barrels 222A-222C and the plungers 223A-223C operate together similar to the way that syringes operate. The plungers 223A-223C can be linearly pulled and pushed along the inside the barrels 222A-222C, allowing the reciprocal pump 116 to draw in and expel liquids through the ports 240A-240C, 241A, and 241C.

As shown, each of the barrels 222A-222C holds a predetermined, different volume. Thus, when the reciprocating pump 116 draws the nutrients, water, and spores, it can draw them in a predetermined, ratioed volume. The controller 150 can direct the reciprocal pump 116 to draw the nutrients, water, and spores in the drawing phase of the system 100 through control of the motor 226. The displacement rod 225 can be embodied as a threaded rod, and the displacement coupling 228 includes threads that engage with those on the displacement rod 225. Thus, when the controller 150 directs the motor 226 to rotate the displacement rod 225 in a first rotational direction, the displacement rod 225 can pull the displacement coupling 228, the mounting bracket 224, and the plungers 223A-223C up in the direction D shown in FIG. 6A, drawing the nutrients, water, and spores. On the other hand, when the controller 150 directs the motor 226 to rotate the displacement rod 225 in a second, opposing rotational direction, the displacement rod 225 can push the displacement coupling 228, the mounting bracket 224, and the plungers 223A-223C down in the direction D shown in FIG. 6A, expelling the nutrients, water, and spores.

To facilitate and mechanically balance the movement of the mounting bracket 224, the mounting bracket 224 is mechanically coupled to the linear displacement bracket 229, which allows the mounting bracket 224 to slide linearly in the direction D. The linear displacement bracket 229 can be mounted to the back of the enclosure 200, for example, to help secure the reciprocating pump 116 in place. The reciprocating pump 116 can be enclosed and mounted or secured in part by the pump enclosure 230 and the pump bracket 231.

Figure 7A:
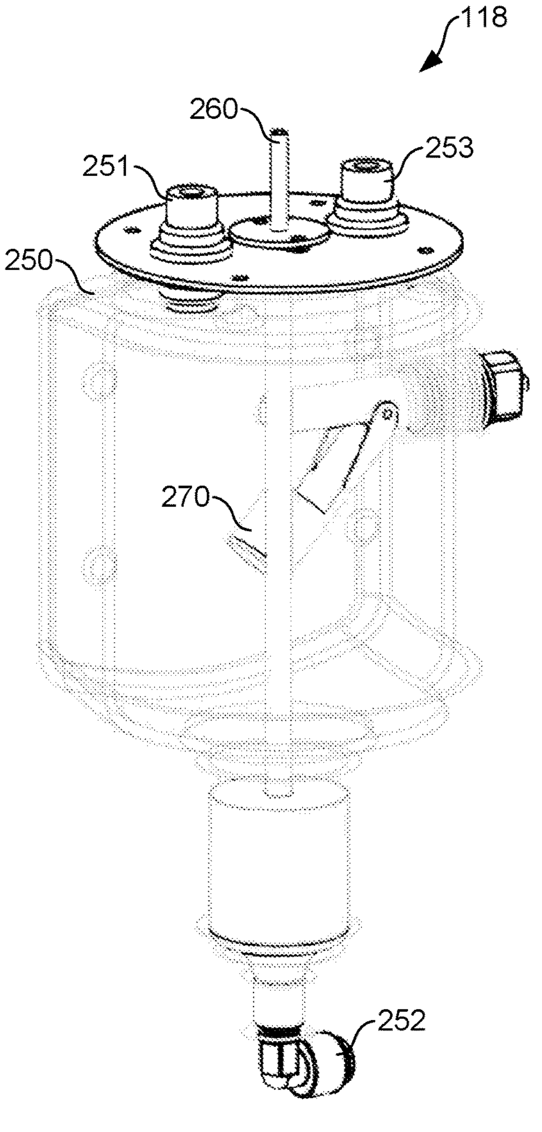
FIGS. 7A and 7B illustrate an example holding tank for the mixing system shown in FIG. 3 according to various embodiments described herein.
Figure 7B:
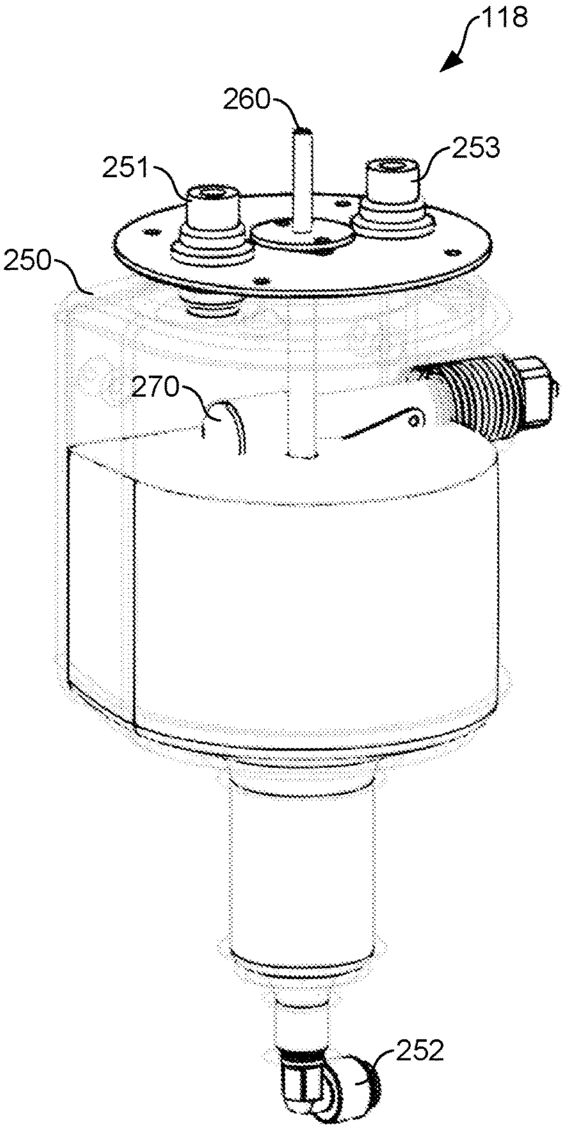

FIG. 7A illustrates an example of the holding tank 118 for the mixing system 100 shown in FIG. 3 with the float switch 270 in a lowered position, and FIG. 7B illustrates the holding tank 118 with the float switch 270 in a raised position. Among other components, the holding tank 118 may include a holding container 250, a heater 260 that extends into the container 250, a float switch 270, an inlet port 251, an outlet port 252, and a vent port 253. In other embodiments, the water can be heated in a separate tank. In that case, the heater 260 could be omitted from the holding tank 118. The float switch 270 can be embodied as any suitable style water sensor or replaced with a flow meter.

The holding container 250 can be formed from any suitable material or materials, such as plastics, glass, or stainless steel or other corrosion resistant non-hydroscopic materials in the industry. As shown in FIG. 7B, the inside surfaces of the holding container 250 slope toward the outlet port 252 without any areas for fluids to pool or become trapped within the holding container 250.

The mixture of nutrients, water, and spores can be pumped through the inlet port 251 and into the holding container 250 by the reciprocating pump 116. As the total volume of fluid pumped during each cycle of the reciprocating pump 116 is known, the controller 150 can direct the reciprocating pump 116 through a number of drawing and expelling phases to fill the holding container 250 to a predetermined, desired level, as described above. Because additional cooling water can be added to the holding container 250 after the mixture is heated, the number of drawing and expelling phases can be selected to fill the holding container 250 to a level below that which would trigger the float switch 270. Then, after the mixture is heated to the predetermined temperature of about 42° Celsius, for example, the controller 150 can fill the holding container 250 with the cooling water until the float switch 270 is tripped.

In one example, the heater 260 can be embodied as a cartridge made of corrosion resistant stainless steel, and the heater 260 can extend directly into the mixture within the holding container 250. In other cases, the heater 260 could heat the outside walls of the holding container 250. For example, a heater could be wrapped around or integrated with the holding container 250 in place of or in addition to the heater 260. Alternatively the heater may heat a separate vessel (e.g., holding oil) to indirectly heat the mixture within the holding container 250. In still other cases, a heater could be placed in a separate tank to deliver hot water to the reciprocating pump 116, and then be delivered from the reciprocating pump 116 into the holding tank 118.

The controller 150 can transition the system 10 to the cooling phase when it detects that the temperature of the mixture in the holding container 250 reaches the predetermined temperature, after the mixture reaches the predetermined temperature for a certain period of time, or at other suitable times. In one example, the controller 150 can flush water into the holding container 250 during the cooling phase until the float switch 270 indicates that the level of fluid in the holding container 250 reaches a certain level as shown in FIG. 7B. At that point, the controller 150 can transition the system 100 to a purging phase. In the purging phase, the controller 150 can direct the feed pump 120 to pump the mixture out of the holding container 250 through the outlet port 252.

In other aspects of the embodiments, the controllers described herein can include at least one processing circuit. Such a processing circuit can include, for example, one or more processors and one or more storage or memory devices that are coupled to a local interface. The local interface can include, for example, a data bus with an accompanying address/control bus or any other suitable bus structure. The storage or memory devices can store data or components that are executable by the processors of the processing circuit.

The controllers described herein and/or other components can be embodied in the form of hardware, as software components that are executable by hardware, or as a combination of software and hardware. If embodied as hardware, the components described herein can be implemented as a circuit or state machine that employs any suitable hardware technology. The hardware technology can include, for example, one or more microprocessors, discrete logic circuits having logic gates for implementing various logic functions upon an application of one or more data signals, application specific integrated circuits (ASICs) having appropriate logic gates, programmable logic devices (e.g., field-programmable gate array (FPGAs), and complex programmable logic devices (CPLDs)).

Also, one or more of the components described herein that include software or program instructions can be embodied in any non-transitory computer-readable medium for use by or in connection with an instruction execution system, such as a processor in a computer system or other system. The computer-readable medium can contain, store, and/or maintain the software or program instructions for use by or in connection with the instruction execution system.

A computer-readable medium can include a physical media (i.e., "non-transitory medium"), such as, magnetic, optical, semiconductor, and/or other suitable devices. Examples of a suitable computer-readable media include, but are not limited to, solid-state drives, magnetic drives, or flash memory. Further, any logic or component described herein can be implemented and structured in a variety of ways. For example, one or more components described can be implemented as modules or components of a single application. Further, one or more components described herein can be executed in one computing device or by using multiple computing devices.

Although embodiments have been described herein in detail, the descriptions are by way of example. The features of the embodiments described herein are representative and, in alternative embodiments, certain features and elements can be added or omitted.

Additionally, modifications to aspects of the embodiments described herein can be made by those skilled in the art without departing from the spirit and scope of the present invention defined in the following claims, the scope of which are to be accorded the broadest interpretation so as to encompass modifications and equivalent structures.

Referring next to FIG. 8, shown is a flowchart that provides one example of the operation of the controller 50 (FIG. 1) according to various embodiments. It is understood that the flowchart of FIG. 8 provides merely an example of the many different types of functional arrangements that may be employed to implement the operation of a portion of the controller 50 as described herein. As an alternative, the flowchart of FIG. 8 may be viewed as depicting an example of elements of a method implemented in the controller 50 according to one or more embodiments.

Beginning with box 803, the controller 50 may initiate a drawing phase. In the drawing phrase, the controller 50 may control the reciprocating pump 16 to draw a ratioed volume of the spores, the nutrients, and water through the valves and tubes 30. In some examples during the drawing phase of the system 10, the controller 50 may control (e.g., open and/or close) one or more valves among the valves and tubes 30 to direct the flow of the nutrients, spores, and water into the pump barrels 22 of the reciprocating pump 16.

In box 806, the controller 50 may initiate an expelling phase. In the expelling phase, the controller 50 may direct the reciprocating pump 16 to expel the nutrients, the spores, and the water back into the valves and tubes 30 and to a mixing tube 31. In box 809, the system 10, via the mixing tube 31, can enable the volume of the solution of spores, the volume of the solution of nutrients, and the volume of water to mix together to form a mixture of the spores, the solution of nutrients, and the water.

In box 812, the system 10 can direct the mixture of the spores, the nutrients, and the water from the mixing tube 31 to a holding tank 18. The controller 50 may control flow control valves to direct the spores, nutrients, and water through the mixing tube 31 and into the holding tank 18.

In box 815, the controller 50 may direct a heater 24 to heat the mixture of the spores, the nutrients, and the water in the holding tank 18. In some examples, the holding tank 18 comprises the heater 24 and a thermocouple 24A to measure a temperature of the mixture in the holding tank 18. The mixture can be heated, in various cases, at a predetermined rate, over a predetermined period of time, and to a predetermined temperature. Once the mixture reaches the target temperature, the controller 50 can also direct the system 10 through a number of other phases of operation, including cooling and purging phases. Due to the heat and the nutrients, the spores in the mixture progress through germination to a type of metastable state in which most of the spores are neither dormant nor in the vegetative growth phase. From that state, the mixture can be mixed into the drinking water of animals (or plants) to facilitate digestion according to one example. Afterward, the controller 50 proceeds to the end as shown.

Therefore, the following is claimed:

1. A system, comprising:

a spore container to store a solution of spores;

a nutrient container to store a solution of nutrients;

an arrangement of valves and tubes;

a reciprocating pump to draw and expel a volume of the solution of spores, a volume of the solution of nutrients, and a volume of water through the arrangement of valves and tubes;

a mixing tube to receive from the reciprocating pump, the mixing tube comprises a mixing spiral for mixing together the volume of the solution of spores, the volume of the solution of nutrients, and the volume of water into a mixture of the solution of spores, the solution of nutrients, and the water;

a holding tank to receive and hold the mixture, the holding tank comprising a heater to heat the mixture and a thermocouple to measure a temperature of the mixture in the holding tank, wherein the mixing tube is in a fluid pathway between the reciprocating pump and the holding tank; and a controller configured to control a sequence of operations among the reciprocating pump and the holding tank to form and activate the mixture.

2. The system of claim 1, wherein the system is on-site.

3. The system of claim 1, wherein the arrangement of valves and tubes comprises a number of flow control valves, a number of check valves, and a number of tubes that form a number of fluid pathways between the spore container, the nutrient container, the reciprocating pump, and the holding tank.

4. The system of claim 3, wherein, in a drawing phase of the system, the controller is configured to:

direct the reciprocating pump to simultaneously draw the solution of spores, the solution of nutrients, and the water into the reciprocating pump; and control at least one of the number of flow control valves to draw the water through a portion of the arrangement of valves and tubes and into the reciprocating pump.

5. The system of claim 3, wherein, in an expelling phase of the system, the controller is configured to:

direct the reciprocating pump to simultaneously expel the solution of spores, the solution of nutrients, and the water out of the reciprocating pump; and control at least one of the number of flow control valves to direct the solution of spores, the solution of nutrients, and the water through a portion of the arrangement of valves and tubes, through the mixing tube, and into the holding tank.

6. The system of claim 3, wherein, in a flushing phase of the system, the controller is configured to control at least one of the number of flow control valves to flush the solution of spores, the solution of nutrients, and the water through a portion of the arrangement of valves and tubes, through the mixing tube, and into the holding tank.

7. The system of claim 3, wherein, in a heating phase of the system, the controller is configured to direct the heater to heat the mixture in the holding tank and to monitor the thermocouple for a target temperature of the mixture.

8. The system of claim 7, wherein, in the heating phase of the system, the controller is configured to direct the heater to heat the mixture in the holding tank and to monitor the thermocouple for a target time.

9. The system of claim 8, wherein, in a cooling phase of the system, the controller is configured to control at least one of the number of flow control valves to flush water into the holding tank and dilute the mixture in the holding tank at a timing based on the target time and the target temperature.

10. The system of claim 7, wherein, in a purging phase of the system, the controller is configured to direct a peristaltic pump to draw the mixture out of the holding tank.

11. The system of claim 10, wherein, in the purging phase of the system, the controller is configured to direct the peristaltic pump to draw the mixture out of the holding tank at a rate for mixing with water for ingestion by a certain animal.

12. The system of claim 1, wherein the reciprocating pump comprises a barrel and a plunger for each of the solution of spores, the solution of nutrients, and the water.

13. The system of claim 12, wherein the barrel and the plunger for each of the solution of spores, the solution of nutrients, and the water that has a different diameter to control a ratio of each.

14. The system of claim 12, wherein the reciprocating pump is configured to draw the solution of spores, the solution of nutrients, and the water to a predetermined ratio of different volumes based on a respective volume of the barrel for each of the solution of spores, the solution of nutrients, and the water.

15. The system of claim 1, wherein the holding tank further comprises an air vent.

16. The system of claim 1, wherein the holding tank further comprises an air vent comprising a filter to isolate a cavity in the holding tank from particles in air.

17. The system of claim 1, wherein the controller is further configured to control the sequence of operations among the reciprocating pump and the holding tank to provide on-site germination of the spores in the mixture.

18. The system of claim 1, wherein the heater is positioned inside of the holding tank.

19. The system of claim 1, wherein the mixing spiral of the mixing tube comprises a first helical twist and a second helical twists that are alternating in a plurality of rotations.

20. The system of claim 1, further comprising:

a feed pump that draws the mixture from the holding tank at a rate configured by the controller, and the feed pump provides to a water distribution system a combination of the mixture and water from a water supply.

* * * * *